(12) United States Patent
Shi

(10) Patent No.: US 11,988,590 B2
(45) Date of Patent: May 21, 2024

(54) METHODS AND DEVICES FOR CORRECTION IN PARTICLE SIZE MEASUREMENT

(71) Applicant: CytoChip Inc., Irvine, CA (US)

(72) Inventor: Wendian Shi, Irvine, CA (US)

(73) Assignee: CytoChip Inc., Irvine, CA (US)

( * ) Notice: Subject to any disclaimer, the term of this patent is extended or adjusted under 35 U.S.C. 154(b) by 302 days.

(21) Appl. No.: 17/594,507

(22) PCT Filed: Apr. 27, 2020

(86) PCT No.: PCT/US2020/030073
§ 371 (c)(1),
(2) Date: Oct. 20, 2021

(87) PCT Pub. No.: WO2020/220019
PCT Pub. Date: Oct. 29, 2020

(65) Prior Publication Data
US 2022/0205897 A1  Jun. 30, 2022

Related U.S. Application Data

(60) Provisional application No. 62/839,090, filed on Apr. 26, 2019.

(51) Int. Cl.
*G01N 15/10* (2006.01)
*G01N 15/0205* (2024.01)
(Continued)

(52) U.S. Cl.
CPC ..... *G01N 15/1012* (2013.01); *G01N 15/0205* (2013.01); *G01N 15/1459* (2013.01);
(Continued)

(58) Field of Classification Search
CPC ........... G01N 15/1012; G01N 15/0205; G01N 15/1459; G01N 33/4915; G01N 2015/0065; G01N 2015/1493; G01N 2015/0053
See application file for complete search history.

(56) References Cited

U.S. PATENT DOCUMENTS 8,383,043 B2   2/2013  Padmanabhan et al.
8,841,117 B2   9/2014  Nagai et al.

FOREIGN PATENT DOCUMENTS

| JP | 2004535570 A | * | 11/2004 |
| WO | 2018098142 A1 | | 5/2018 |
| WO | 2018231835 A1 | | 12/2018 |

OTHER PUBLICATIONS

International Search Report and Written Opinion, dated Jul. 22, 2020, 13 pages, issued in PCT Application No. PCT/US2020/030073.

* cited by examiner

*Primary Examiner* — Kiho Kim
(74) *Attorney, Agent, or Firm* — AVEK IP, LLC

(57) ABSTRACT

Methods and devices for correction in particle size measurement are disclosed. In some embodiments, a method includes the following steps: (1) measuring a signal from a target particle and a reference particle in a cartridge device; (2) analyzing the measured signal to obtain signal information of the target particle and signal information of the reference particle; and (3) determining size information of the target particle by correcting the signal information of the target particle with the signal information of the reference particle. In other embodiments, a device includes a cartridge and an analyzer. The analyzer is configured to receive the cartridge into the analyzer, measure a signal from the target particle and the reference particle, analyze the measured (Continued)

signal to obtain signal information, and determine size information of the target particle.

20 Claims, 16 Drawing Sheets

(51) Int. Cl.
 *G01N 15/14* (2006.01)
 *G01N 33/49* (2006.01)
 *G01N 15/01* (2024.01)
(52) U.S. Cl.
 CPC ......... *G01N 33/4915* (2013.01); *G01N 15/01* (2024.01); *G01N 2015/1493* (2013.01)

Beam spot is aligned with flow cell

Beam spot is misaligned with flow cell

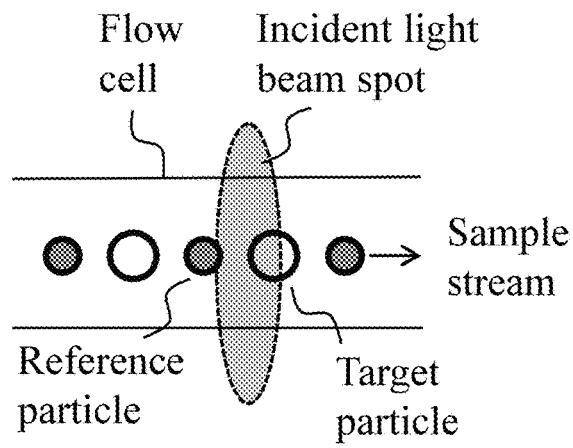
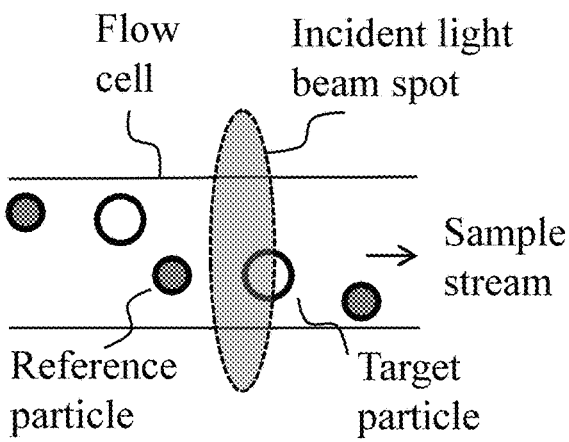
FIG. 7A  FIG. 7C
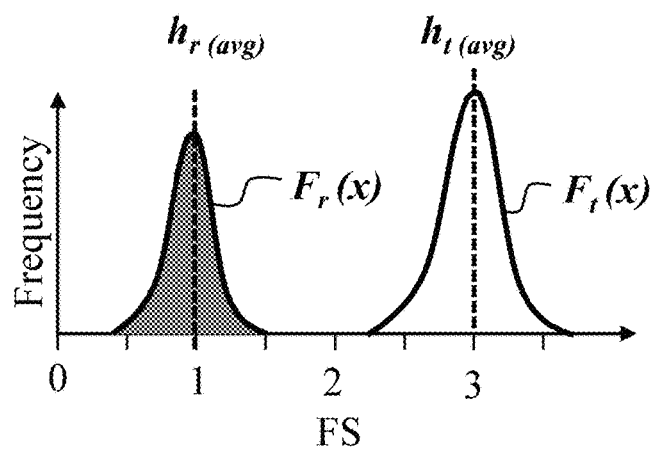
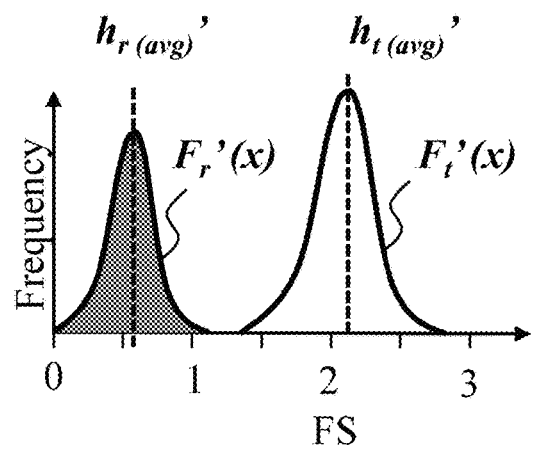
FIG. 7B  FIG. 7D

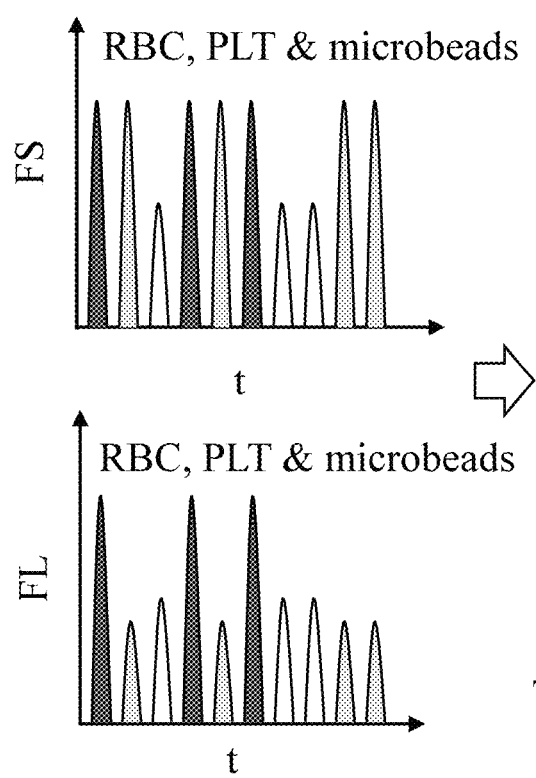 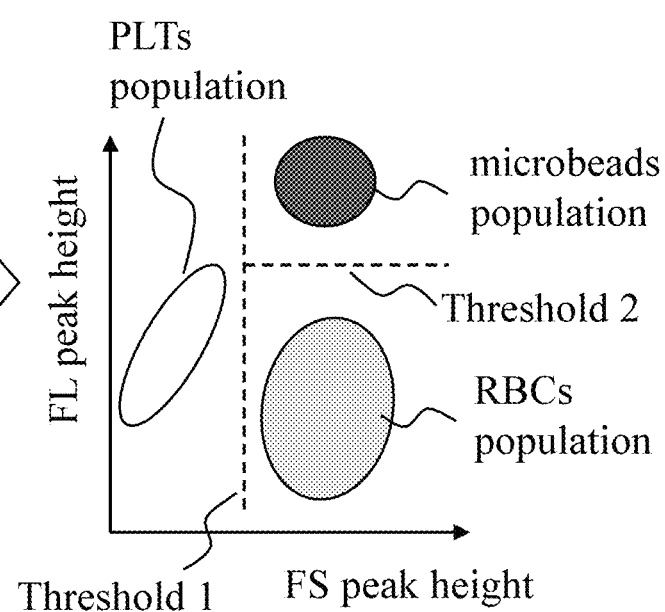
FIG. 12A  FIG. 12B

METHODS AND DEVICES FOR CORRECTION IN PARTICLE SIZE MEASUREMENT

CROSS REFERENCE TO RELATED APPLICATIONS

This application is the United State national stage entry under 37 U.S.C. 371 of PCT/US2020/030073 filed on Apr. 27, 2020, which claims priority to U.S. provisional application No. 62/839,090 filed on Apr. 26, 2019, the disclosure of which are incorporated by reference herein in their entireties.

FIELD OF THE DISCLOSURE

The disclosure relates generally to medicine and cytometry. More specifically, the disclosure relates to methods and devices for correction in particle size measurement.

BACKGROUND

There are many types of particles, for example, solid phase particles (e.g., microbeads, et cetera), liquid phase particles (e.g., liquid droplets, et cetera), and biological particles (e.g., cells and proteins, et cetera.) The size information of particles (e.g., particle diameter and particle volume, et cetera) is determined across a wide range of industries such as healthcare and environmental monitoring. Various types of samples (e.g., liquid samples, gas samples, and biological samples, et cetera) that contain particles can be measured and analyzed. For example, healthcare professionals often use a sample of body fluid (e.g., blood, lymph, sweat, tear, semen, saliva, and urine, et cetera.)

Various types of signals (e.g., optical, acoustic, and electrical signals, et cetera) can be used to determine the size information of particles. Optical signals are used in many technologies, for example, spectrophotometry, dynamic light scattering, laser diffraction, and flow cytometry. Among these, flow cytometry is widely used to determine the size information of particles. Usually, flow cytometry uses a flow cell illuminated by an incident light beam. A sample stream of particles passes through the flow cell, and a signal (e.g., light scattering and fluorescence, et cetera) from those passing particles is measured. The measured signal can be used to analyze various aspects of the size information of the particles in the sample, such as the size of individual particles, sizes of a plurality of particles, the average size of a plurality of particles, and the size distribution of a plurality of particles.

In healthcare, the size information of blood cells is often determined to guide medical decisions. For example, in the laboratory test of Complete Blood Count (CBC), the size information of Red Blood Cells (RBCs), Platelet (PLTs), and White Blood Cells (WBCs) is often determined using flow cytometry. The determined size information includes but is not limited to the size of individual RBCs, the average size of a plurality of RBCs (i.e., Mean Corpuscular Volume MCV), the size distribution of a plurality of RBCs (i.e., Red Cell Distribution Width RDW), the volume percentage of RBCs in blood (i.e., Hematocrit HCT), the average size of a plurality of platelets (i.e., Mean Platelet Volume MPV), the size distribution of a plurality of PLTs (i.e., Platelet Distribution Width PDW), and the volume percentage of PLTs in blood (i.e., Plateletcrit), et cetera In recent years, new healthcare applications such as point-of-care testing (POCT) require new methods and devices for particle size measurement. These new methods and devices often use a disposable fluidic cartridge and an analyzer to perform the measurement. For example, a device including a cartridge and an analyzer can apply flow cytometry to determine the size information of particles. A sample containing particles is loaded into a cartridge that has a flow cell, and the cartridge is placed in an analyzer. The analyzer illuminates the flow cell with an incident light beam, measures signals from the particles passing through the flow cell and analyze their size information.

However, there are many challenges to use a cartridge and an analyzer to perform size measurement. For one example, when the cartridge is placed in the analyzer, the alignment between the cartridge's flow cell and the analyzer's incident light beam varies from time to time. This variation in alignment causes variation in signal measurement and leads to inconsistency in the size information of the same particle analyzed at different times. For another example, when particles pass through the flow cell, their positioning in the flow cell may vary. The variation in positioning can be significant when the flow cell has a cross section size larger than the particles or when there is no sheath flow to focus the particles. This variation in positioning also causes variation in signal measurement and leads to inconsistency in the size information of the same particle analyzed at different times.

U.S. Pat. No. 5,084,394 described a method of adjusting a flow cytometer with reference microbeads, but it did not teach using reference particles for size correction of target particles. U.S. Pat. No. 5,747,349 described a method of using flow cytometry and beads for determining analyte concentrations, but it did not teach size measurement of particles. U.S. Pat. No. 7,688,427 described a method of using flow cytometry for measuring the size of particles in a cartridge, but it did not teach a size correction using reference particles. U.S. Pat. No. 7,641,856 described a method of using a calibration cartridge to adjust a flow cytometer, but it did not teach using reference particles for size correction of target particles.

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

In some embodiments, the disclosure provides a method including the following steps. (1) Measuring a signal from a target particle and a reference particle in a cartridge device. The cartridge device is received into an analyzer to perform the measurement of the signal, and the signal is measured from the target particle and the reference particle when they flow through a flow cell in the cartridge device. (2) Analyzing the measured signal to obtain signal information of the target particle and signal information of the reference particle. (3) Determining size information of the target particle by correcting the signal information of the target particle with the signal information of the reference particle.

Optionally, the reference particle has a known size.

Optionally, two or more types of signals are measured to distinguish the signal information of the target particle from the signal information of the reference particle.

Optionally, the measured signal includes an optical signal, an electrical signal, an acoustic signal, a magnetic signal, or a combination thereof. The optical signal includes a forward scattering signal, a fluorescence signal, or a combination thereof.

Optionally, the obtained signal information includes a peak height, a peak width, a peak area, an averaged peak height, an average peak width, an average peak area, a distribution of peak heights, a distribution of peak widths, a distribution of peak areas, a distribution width of peak heights, or a combination thereof.

Optionally, the determined size information includes a particle diameter, a particle volume, an average particle diameter, an average particle volume, a distribution of particle diameters, a distribution of particle volumes, or a combination thereof.

Optionally, the flow cell is a sheathless flow cell.

Optionally, the reference particle is stored in the cartridge device before the target particle is received into the cartridge device.

Optionally, the reference particle and the target particle form a sample mixture in the cartridge device before flowing through the flow cell.

Optionally, the cartridge further contains a fluorescent dye configured to label the target particles or a surfactant. The sample mixture includes: (a) a combination of the fluorescent dye, the reference particle, and the target particle, or (b) a combination of the surfactant, the reference particle, and the target particle.

Optionally, the target particle is a blood cell.

Optionally, the determined size information includes at least one item selected from the list consisting of: Mean Corpuscular Volume (MCV), Red Cell Distribution Width (RDW)), Hematocrit (HCT), Mean Platelet Volume (MPV), Platelet Distribution Width (PDW), plateletcrit, averaged size of Monocyte, and Monocyte width distribution (MWD) of a sample including blood cells.

In other embodiments, the disclosure provides a device including a cartridge and an analyzer. The analyzer is configured to: receive the cartridge into the analyzer; measure a signal from a target particle and a reference particle when the target particle and the reference particle flow through a flow cell in the cartridge; analyze the measured signal to obtain signal information of the target particle and signal information of the reference particle; and determine size information of the target particle by correcting the signal information of the target particle with the signal information of the reference particle.

Optionally, the reference particle has a known size.

Optionally, the cartridge includes a reference particle and is configured to form a sample mixture of the target particle and the reference particle.

Optionally, the cartridge further includes a fluorescent dye configured to label the target particle or a surfactant. The cartridge is configured to form: (a) a sample mixture of the target particle, the reference particle, and the fluorescent dye, or (b) a sample mixture of the target particle, the reference particle, and the surfactant.

Optionally, the flow cell is a sheathless flow cell.

Optionally, the measured signal includes an optical signal, an electrical signal, an acoustic signal, a magnetic signal, or a combination thereof. The optical signal includes a forward scattering signal, a fluorescence signal, or a combination thereof.

Optionally, the determined size information includes a particle diameter, a particle volume, an average particle diameter, an average particle volume, a distribution of particle diameters, a distribution of particle volumes, a distribution width of peak heights, or a combination thereof.

Optionally, the target particle is a blood cell.

BRIEF DESCRIPTION OF THE DRAWINGS

Illustrative embodiments of the disclosure are described in detail below with reference to the figures.

FIG. 7A illustrates an example of measuring a plurality of target particles and a plurality of reference particles in a flow cell when all the particles pass through the center of the flow cell according to an embodiment of the disclosure.

FIG. 7B illustrates an example of distinguishing the size information of the target particles from the size information of the reference particles using a histogram of FS peak heights according to an embodiment of the disclosure.

FIG. 7C illustrates an example of measuring a plurality of target particles and a plurality of reference particles in a flow cell when the particles pass through various positions of the flow cell according to an embodiment of the disclosure.

FIG. 7D illustrates an example of distinguishing the size information of the target particles from the size information of the reference particles using a histogram of FS peak heights. according to an embodiment of the disclosure

FIGS. 12A-12B illustrate another example of determining the size information of blood cells with correction where the target particles are RBCs and PLTs, and the reference particles are microbeads according to an embodiment of the disclosure.

DETAILED DESCRIPTION

Figure 1:
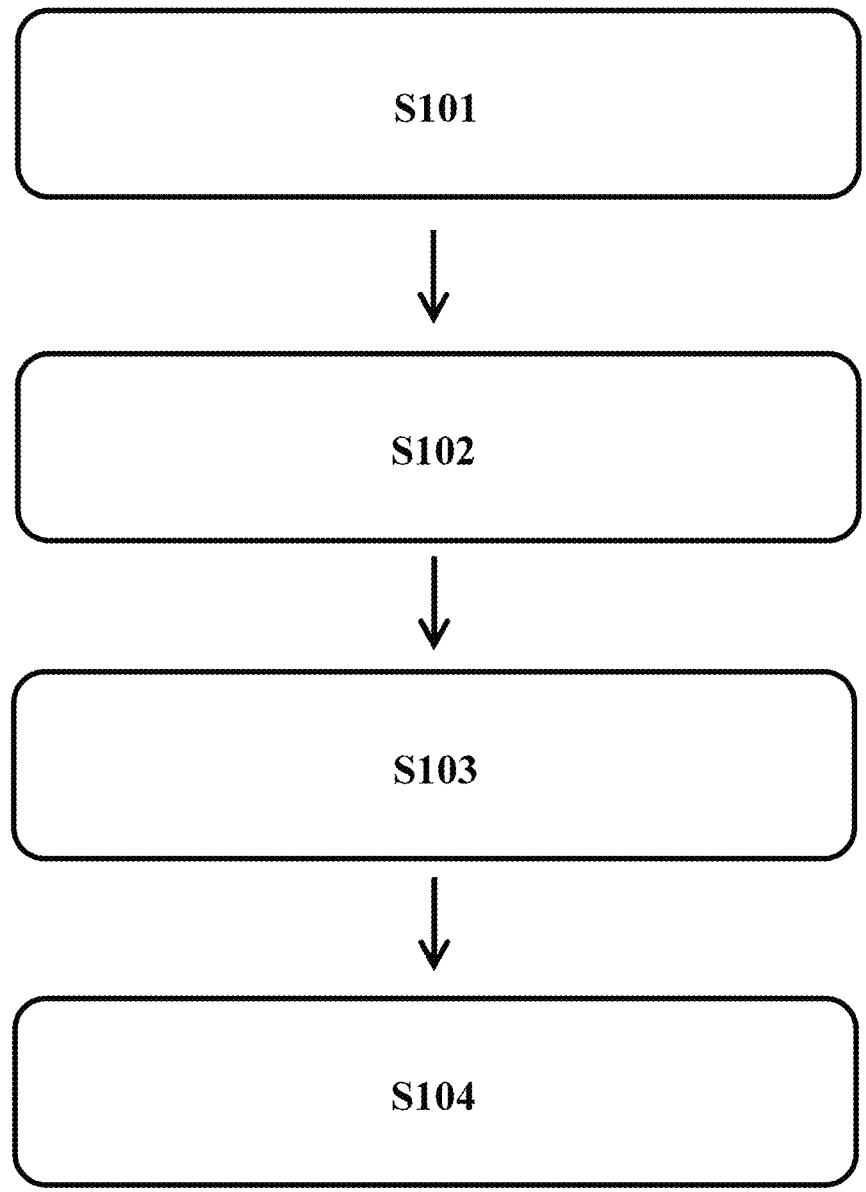
FIG. 1 is a block diagram illustrating a method of determining the size information of target particles with correction from reference particles according to an embodiment of the disclosure.

The following describes some non-limiting embodiments of the invention with reference to the accompanying drawings. The described embodiments are merely a part rather than all of the embodiments of the invention. All other embodiments obtained by a person of ordinary skill in the art based on the embodiments of the disclosure shall fall within the scope of the disclosure.

In various embodiments, the disclosure provides a method of determining the size information of target particles. The method includes: measuring a signal from a target particle and a reference particle in a cartridge; analyzing the measured signal to obtain signal information of the target particle and a signal information of the reference particle; and determining the size information of the target particle by correcting the signal information of the target particle with the signal information of the reference particle. In various embodiments, the method further includes distinguishing the signal information of the target particle from the signal information of the reference particle. In some embodiments, one or more of these steps (e.g., measuring a signal, analyzing the measured signal, and determining the size information) are performed by an analyzer. In certain embodiments, the analyzer is configured for receiving the cartridge and the method further includes receiving the cartridge into the analyzer.

In various embodiments, the disclosure provides a method of determining the size information of target particles. The method includes: receiving a cartridge into an analyzer; using the analyzer to measure a signal from a target particle and a reference particle in the cartridge; analyzing the measured signal to obtain signal information of the target particle and a signal information of the reference particle; and determining the size information of the target particle by correcting the signal information of the target particle with the signal information of the reference particle. In various embodiments, the method further includes distinguishing the signal information of the target particle from the signal information of the reference particle.

In various embodiments, the disclosure provides a device for determining the size information of target particles. The device includes: a cartridge and an analyzer. The analyzer is configured for: receiving the cartridge into the analyzer; measuring a signal from the target particle and the reference particle in the cartridge; analyzing the measured signal to obtain signal information of the target particle and a signal information of the reference particle; and determining the size information of the target particle by correcting the signal information of the target particle with the signal information of the reference particle. In various embodiments, the analyzer is further configured for distinguishing the signal information of the target particle from the signal information of the reference particle. In some embodiments, the analyzer is further configured for measuring two or more types of signals to distinguish the signal information of the target particle from the signal information of the reference particle.

In various embodiments, the cartridge includes a flow cell configured for a target particle and a reference particle to pass through. In various embodiments, the signal is measured from the target particle and the reference particle when they pass through a flow cell in the cartridge.

In various embodiments, the cartridge is configured to form a sample mixture of the target particle and the reference particle.

In various embodiments, the cartridge includes a reference particle and is configured to form a sample mixture of the target particle and the reference particle. In various embodiments, the cartridge includes a plurality of reference particles. In various embodiments, the cartridge includes two or more types of reference particles. For example, the reference particles may have various sizes, various fluorescence intensities, and various fluorophores, as compared to simply having one size, one fluorescence intensity and one fluorophore.

In various embodiments, the cartridge further includes a surfactant and is configured to form a sample mixture of the target particle, the reference particle, and the surfactant.

In various embodiments, the cartridge further includes a fluorescent dye and is configured to form a sample mixture of the target particle, the reference particle, and the fluorescent dye.

In various embodiments, the cartridge further includes a fluorescent dye configured to label the target particle or a surfactant. The cartridge is configured to form: (a) a sample mixture of the target particle, the reference particle, and the fluorescent dye, or (b) a sample mixture of the target particle, the reference particle, and the surfactant.

In various embodiments, the signal is measured from the target particle and the reference particle after they form a sample mixture. In various embodiments, the signal is measured from the target particle and the reference particle after they form a sample mixture with a surfactant.

In various embodiments, the signal is measured from the target particle and the reference particle after they form a sample mixture. In various embodiments, the signal is measured from the target particle and the reference particle after they form a sample mixture with a fluorescent dye. And the signal measured from the target particle include a signal of fluorescence intensity.

In various embodiments, the measured signal includes an optical signal, an electrical signal, an acoustic signal, or a magnetic signal, or a combination thereof. In various embodiments, the optical signal includes a forward scattering signal, or a fluorescence signal, or a combination thereof. In some embodiments, two or more types of signals are measured to distinguish the signal information of the target particle from the signal information of the reference particle.

In various embodiments, the obtained signal information includes the peak height, the peak width, the peak area, the averaged peak height, the average peak width, the average peak area, the distribution of peak heights, the distribution of peak widths, or the distribution of peak areas, or a combination thereof.

In various embodiments, the determined size information includes the particle diameter, the particle volume, the average particle diameter, the average particle volume, the distribution of particle diameters, or the distribution of particle volumes, or a combination thereof.

In various embodiments, the reference particle has a known size.

In various embodiments, the target particle is a blood cell. In various embodiments, the determined size information includes at least one item selected from the list consisting of: Mean Corpuscular Volume (MCV), Red Cell Distribution Width (RDW), Hematocrit (HCT), Mean Platelet Volume (MPV), Platelet Distribution Width (PDW), and plateletcrit of a sample including blood cells.

FIG. 1 shows a non-limiting example of a method to determine the size information of particles. First in step S101, a signal is measured from a sample having particles. Second in step S102, the signal is analyzed to obtain a signal information of the particles. Third in step S103, the signal information of a target particle is distinguished from the signal information of a reference particle. Fourth in step S104, the size information of the target particle may be determined by correcting the signal information of the target particle with the signal information of the reference particle.

Figure 2A:
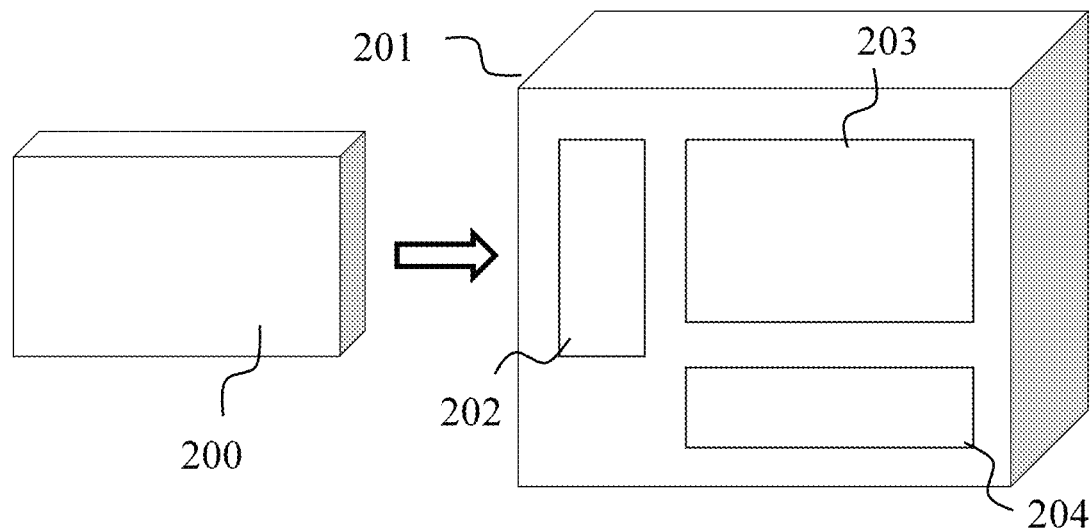
FIG. 2A illustrates a device having a cartridge and an analyzer to measure the size information of particles according to an embodiment of the disclosure.
Figure 2B:
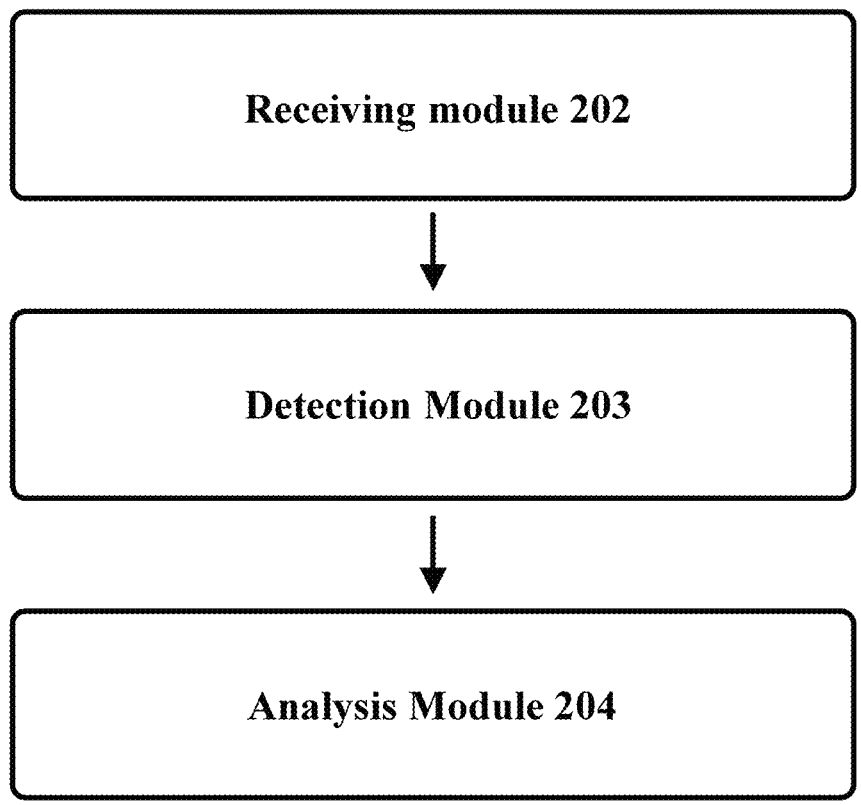
FIG. 2B is a block diagram illustrating a process implemented in the device as shown in FIG. 2A.

FIG. 2A shows a non-limiting example of a device for determining the size information of particles. The device may include a cartridge 200 and an analyzer 201. The analyzer 201 receives the cartridge, measures a signal from the particles in the cartridge, analyzes the signal to obtain a signal information, and uses the signal information to determine the size information of the particles. In this example, the analyzer 201 has three modules as shown in FIG. 2B. A receiving module 202 receives the cartridge 200 into the analyzer 201. A detection module 203 detects a signal from the particles in the cartridge 200. An analysis module 204 analyzes the signal detected by the detection module 203 to obtain a signal information, distinguishes the signal information of a target particle from the signal information of a reference particle, and determines the size information of the target particle.

Figure 3A:
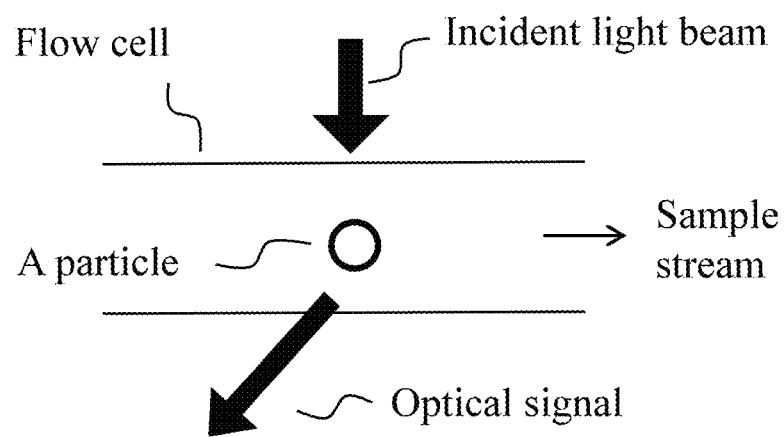
FIG. 3A illustrates an example of measuring an optical signal from a particle in a flow cell according to an embodiment of the disclosure.
Figure 3B:
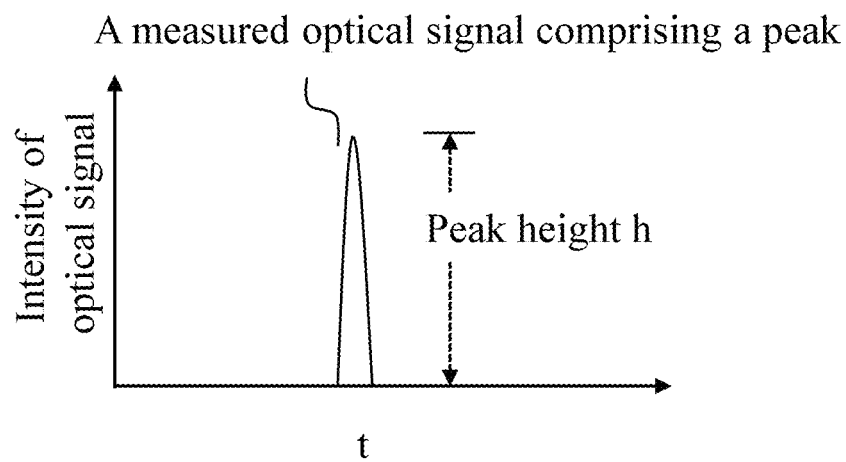
FIG. 3B illustrates an example of analyzing an optical signal to obtain signal information according to an embodiment of the disclosure.
Figure 4A:
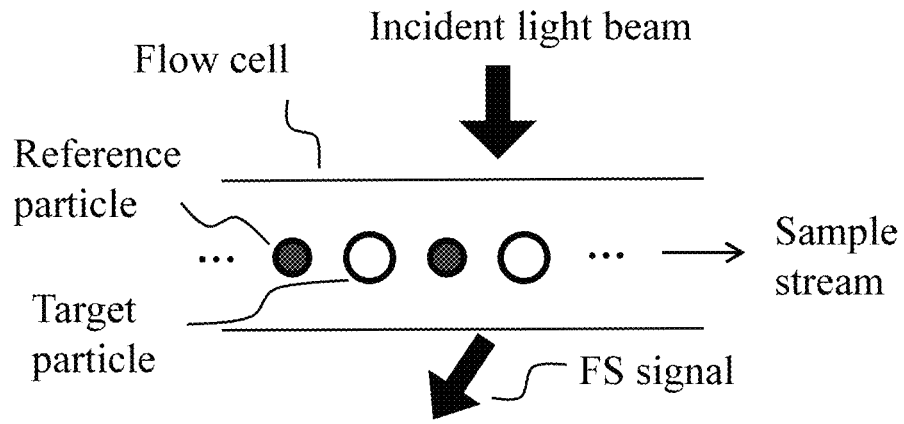
FIG. 4A illustrates an example of reference particles and target particles of different sizes passing through a flow cell while being illuminated by an incident light beam and generating an optical forward scattering (FS) signal according to an embodiment of the disclosure.
Figure 4B:
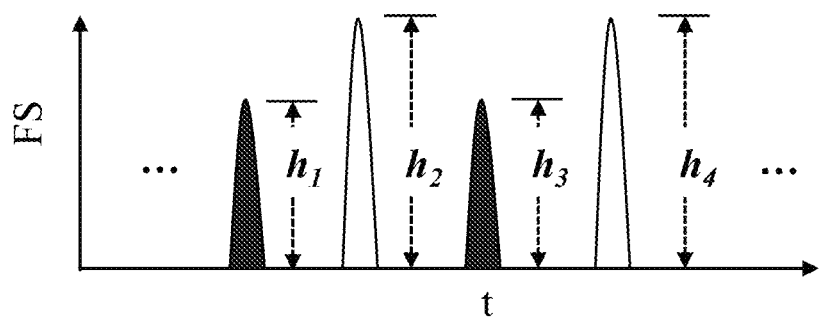
FIG. 4B illustrates an example of obtaining FS peak heights and peak numbers as the signal information according to an embodiment of the disclosure.
Figure 4C:
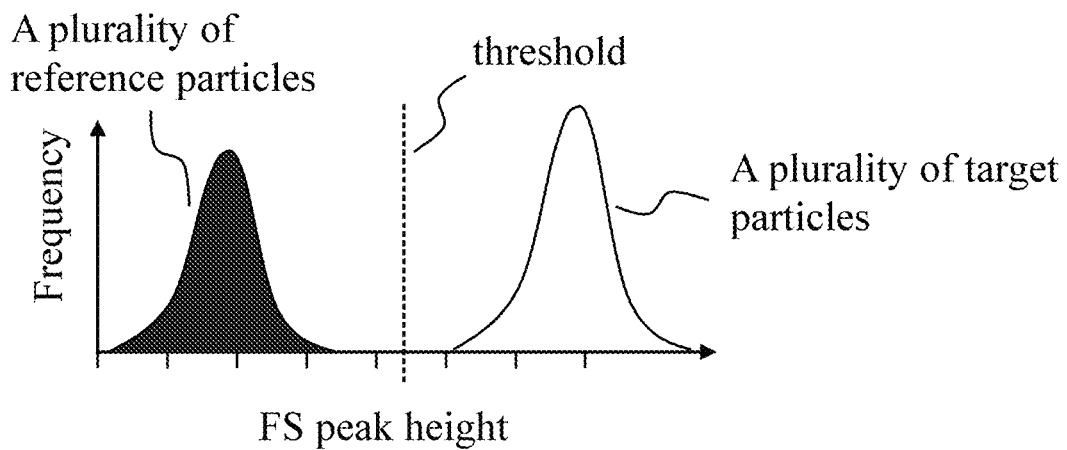
FIG. 4C illustrates an example of distinguishing the signal information of target particles from the signal information of reference particles by plotting a histogram of FS peak heights versus FS peak frequencies according to an embodiment of the disclosure.

FIG. 3A shows a non-limiting example of how to measure a signal from particles in a cartridge. The cartridge may include a flow cell where a portion of the flow cell is illuminated by an incident light beam from an analyzer. When a sample having particles passes through the illuminated area of the flow cell, an optical signal that contains the size information of the passing particles is measured by a detection module of the analyzer. The measured signal is sent to an analysis module of the analyzer. A peak may be detected in the measured signal when a particle passes through the illuminated area. Multiple peaks may be detected in the measured signal when multiple particles pass through the illuminated area. Non-limiting examples of the optical signal that may be used to determine the size information may include forward scattering light, side scattering light, and fluorescence light, et cetera For one example, when forward scattering light is used, larger particles scatter more incident light and generate signal peaks with higher intensity than smaller particles. For another example, when fluorescence light is used, larger particles contain more fluorophores to emit fluorescence light and generate signal peaks with higher intensity than smaller particles. Various other types of signal that may be used to determine the size information may include but are not limited to electrical signal (e.g., impedance), acoustic signal, and magnetic signal, et cetera FIG. 3B shows a non-limiting example of how to analyze the measured signal and obtain a signal information from the measured signal. The peak number N (N=1 in this example) and the peak height h may be obtained as the signal information of the passing particles. Other signal information that may also be obtained may include but is not limited to the area size of the peak, the width of the peak, and the full-width-at-half-maximum of the peak, et cetera FIGS. 4A-4C show a non-limiting example of how to measure a signal, analyze the signal to obtain a signal information, and distinguish the signal information of a target particle from the signal information of a reference particle. A cartridge for receiving a sample may include a flow cell, and a portion of the flow cell is illuminated by an incident light beam from an analyzer when the cartridge is placed in the analyzer. When a sample having particles passes through the illuminated area of the flow cell, an optical forward scattering (FS) signal is measured by a detection module in the analyzer (FIG. 4A). The FS signal is sent to an analysis module in the analyzer. Each particle passing through the illuminated area of the flow cell corresponds to a peak in the FS signal. The number of FS peaks N and height of each FS peak ($h_i$, i=1, 2, 3, . . . , N) may be obtained as the signal information of the passing particles (FIG. 4B). To distinguish the signal information of the reference particles from the signal information of the target particles, a histogram of the frequency of the FS peaks versus the height of FS peaks may be obtained (FIG. 4C). Two populations may be distinguished from each other in the histogram by setting a threshold of peak height. Because the sizes of reference particles are smaller than sizes of the target particles in this example, the population with peak heights smaller than the threshold is identified as the reference particles. The number of peaks $N_r$ and height of each peak ($h_{r\ (j)}$, j=1, 2, 3, . . . , $N_r$) in this population may be obtained as the signal information of the reference particles. Additionally, signal information such as the average FS peak height of the reference particles $h_{r\ (avg)}$ may be calculated by the following equation (1).

$$h_{r(avg)} = \frac{\sum_{j=1}^{N_r} h_{r(j)}}{N_r} \tag{1}$$

Meanwhile, the population with peak heights larger than the threshold is identified as the target particles. The number of peaks $N_t$ and height of each peak ($h_{t\ (k)}$, k=1, 2, 3, . . . , $N_t$) in this population may be obtained as the signal information of the target particles. Similarly, the average FS peak height of the target particles $h_{t\ (avg)}$ may be calculated by the following equation (2).

$$h_{t(avg)} = \frac{\sum_{k=1}^{N_t} h_{t(k)}}{N_t} \tag{2}$$

Figure 5A:
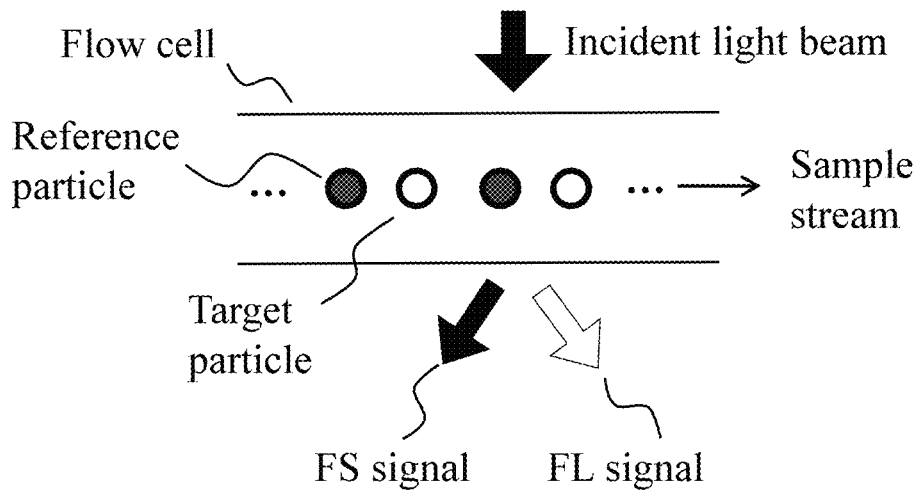
FIG. 5A illustrates an example of reference particles and target particles of similar sizes passing through a flow cell while being illuminated by an incident light beam and generating an FS signal and a fluorescence (FL) signal according to an embodiment of the disclosure.
Figure 5B:
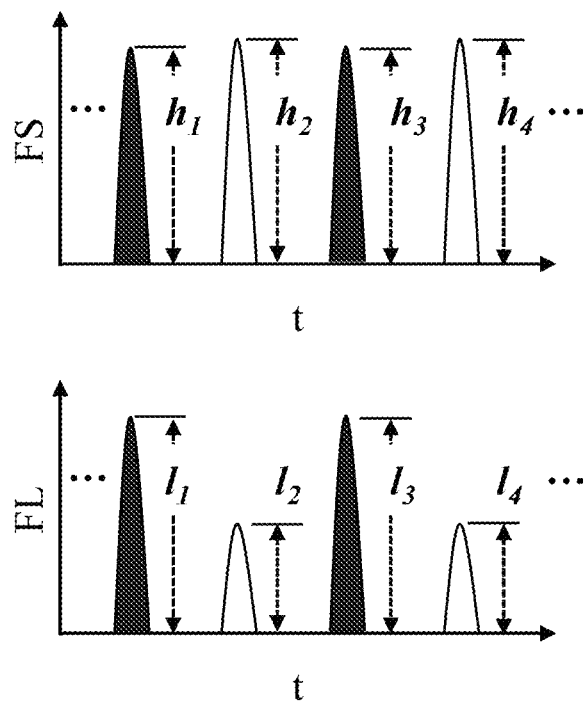
FIG. 5B illustrates an example of obtaining FS peak heights, FL peak heights, and their numbers as the signal information according to an embodiment of the disclosure.
Figure 5C:
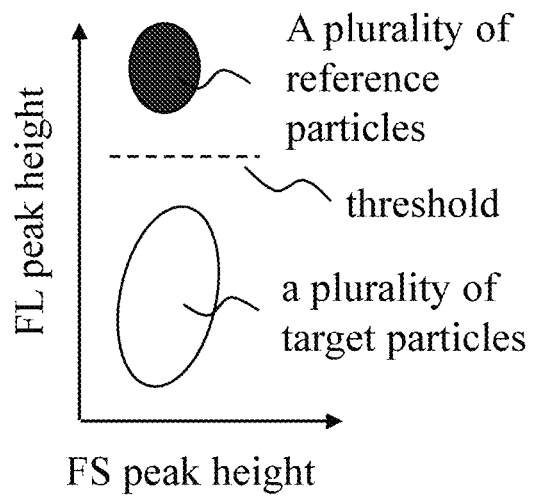
FIG. 5C illustrates an example of distinguishing the signal information of target particles from the signal information of reference particles by plotting a scatter plot of FL peak heights versus FS peak heights according to an embodiment of the disclosure.

FIGS. 5A-5C show another non-limiting example of how to measure a signal, analyze the signal to obtain a signal information, and distinguish the signal information of a target particle from the signal information of a reference particle. A cartridge for receiving a sample may include a flow cell, and a portion of the flow cell is illuminated by an incident light beam from an analyzer when the cartridge is placed in the analyzer. When a sample having particles passes through the illuminated area of the flow cell, an FS signal, and a fluorescence (FL) signal are simultaneously measured by a detection module in the analyzer (FIG. 5A). Both the measured FS signal and the measured FL signal are sent to an analysis module in the analyzer. Each pair of a peak in the FS signal and a peak in the FL signal corresponds to a particle passing through the illuminated area of the flow cell. The number of FS peaks $N_{FS}$ and height of each FS peak ($h_i$, i=1, 2, 3, . . . , $N_{FS}$) in the FS signal may be obtained as the FS signal information. The number of FL peaks $N_{FL}$ and height of each FL peak ($l_i$, i=1, 2, 3, . . . , $N_{FL}$, $N_{FL}=N_{FS}$) in the FL signal may be obtained as the FL signal information (FIG. 5B). A scatter plot of the FL peak height $l_i$ of the measured particles versus the FS peak height $h_i$ may be obtained (FIG. 5C). In this example, two populations may be distinguished from each other by setting a threshold of the FL peak height in the scatter plot. The population with FL peak height larger than the threshold is from the reference particles because the reference particles have stronger FL intensity than the target particles in this example. The number of FS peaks $N_r$ and height of each FS peak ($h_{r\ (j)}$, j=1, 2, 3, . . . , $N_r$) in this population may be obtained as the FS signal information of the reference particles. Additionally, the average FS peak height of the reference particles $h_{r\ (avg)}$ may be obtained with equation (1) described above. Meanwhile, the other population with FL peak heights smaller than the threshold is from the target particles. The number of FS peaks $N_t$ and height of each FS peak ($h_{t\ (k)}$, k=1, 2, 3, . . . , $N_t$) in this population may be obtained as the FS signal information of the target particles. Similarly, the average FS peak height of the target particles $h_{t\ (avg)}$ may be obtained by the equation (2) described above.

Figure 6A:
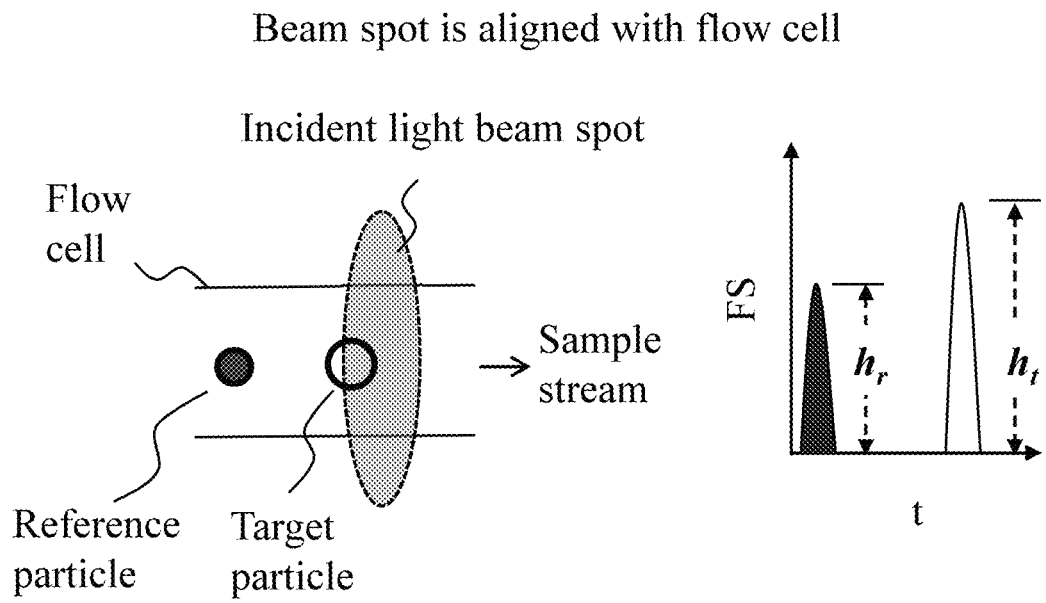
FIG. 6A illustrates an example of measuring a target particle and a reference particle in a flow cell when an incident light beam is aligned with the flow cell according to an embodiment of the disclosure.
Figure 6B:
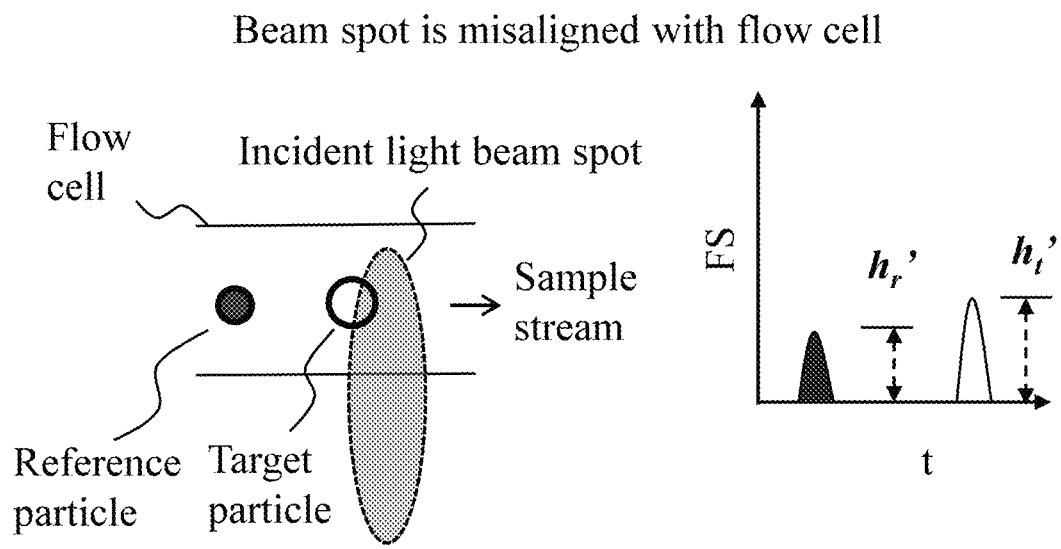
FIG. 6B illustrates an example of measuring a target particle and a reference particle in a flow cell when an incident light beam is misaligned with the flow cell according to an embodiment of the disclosure.

FIGS. 6A-6B show some non-limiting examples of a method of determining the diameter of a target particle $D_t$. In FIG. 6A, a target particle and a reference particle pass through the flow cell and are illuminated by an incident light beam. In this example, the incident light beam is aligned with the center of the flow cell. An FS signal is measured and analyzed to obtain the FS peak height of the target particle $h_t$ and the FS peak height of the reference particle $h_r$. The diameter of the target particle $D_t$ may be determined by correcting $h_t$ of the target particle with $h_r$ of the reference particle as shown in the following equation (3) where $D_r$ is a known diameter of the reference particle.

$$D_t = \frac{h_t}{h_r} \times D_r \tag{3}$$

In FIG. 6B, a target particle and a reference particle pass through the flow cell and are illuminated by an incident light beam. In this example, the incident light beam is misaligned with the center of the flow cell. An FS signal is measured and analyzed to obtain the FS peak height of the target particle $h_t'$ and the FS peak height of the reference particle $h_r'$. The diameter of the target particle in this example $D_t'$ may be determined by correcting $h_t'$ of the target particle with $h_r'$ of the reference particle as shown the following equation (4) where $D_r$ is a known diameter of the reference particle.

$$D_t' = \frac{h_{t'}}{h_{r'}} \times D_r \tag{4}$$

The $h_t'$ measured in FIG. 6B may be different from the $h_t$ measured in FIG. 6A because the incident light beam in FIG. 6B is not aligned with the center of the flow cell. For example, when the incident light beam has a higher intensity at the beam center and lower intensity at the beam edge, the $h_t'$ measured in FIG. 6B is smaller than $h_t$ measured in FIG. 6A. When the FS peak height is used to determine the diameter of the target particle without using a reference particle as described in the disclosure, the difference between $h_t'$ and $h_t$ may result in inconsistent measurements of the diameter of the same target particle. When a cartridge is received into an analyzer, misalignment may happen frequently and therefore lead to inconsistent measurements. This inconsistency may be reduced or avoided using a method as described in the disclosure. For example, the determined diameter $D_t$ may be equal to $D_t'$ when the correction for FIG. 6A and for FIG. 6B are the same as shown in the following equation (5). This may be achieved by having a reference particle and a target particle to pass through the same position of the flow cell.

$$\frac{h_{t'}}{h_{r'}} = \frac{h_t}{h_r} \tag{5}$$

FIGS. 7A-7D show some non-limiting examples of a method of determining the average size or volume of a plurality of target particle $V_{t\ (avg)}$. In FIG. 7A, when a plurality of target particles and reference particles pass through the flow cell illuminated with the incident light beam, all the particles are aligned at the center of the flow cell. An FS signal is measured and analyzed, and the number of FS peaks N and height of each FS peak ($h_i$, i=1, 2, 3, ..., N) may be obtained as the signal information of the passing particles. A histogram of the frequency of FS peaks versus the heights of the FS peaks may be obtained (FIG. 7B). Two populations may be distinguished from each other by setting a threshold of FS peak height in the histogram. The population with peak heights smaller than the threshold is identified as the reference particles, and the number of peaks $N_r$ and height of each peak ($h_{r\,(j)}$, j=1, 2, 3, ..., $N_r$) may be obtained as the signal information of the reference particles. The average FS peak height of the reference particles $h_{r\,(avg)}$ may be obtained with equation (1). Meanwhile, the other population with peak heights larger than the threshold is identified as the target particles, and the number of peaks $N_t$ and height of each peak ($h_{t(k)}$, k=1, 2, 3, ..., $N_t$) may be obtained as the signal information of the target particles. The average FS peak height of the target particles $h_{t\,(avg)}$ may be obtained with equation (2). Accordingly, the average volume of the target particles $V_{t\,(avg)}$ may be determined by correcting $h_{t\,(avg)}$ with $h_{r\,(avg)}$ as shown in the following equation (6) where $V_{r\,(avg)}$ is a known average volume of the reference particles.

$$V_{t(avg)} = \frac{h_{t(avg)}}{h_{r(avg)}} \times V_{r(avg)} \tag{6}$$

When the flow cell has a size of cross section larger than the size of the particles or there is no sheath flow to focus the particles, it is difficult to keep all the particles aligned at the center of the flow cell. Instead, the particles will pass through the flow cell at different positions. As shown in FIG. 7C, when the target particles and reference particles pass through the flow cell at various positions, an FS signal is measured and the number of FS peaks N and height of each FS peak ($h_i'$, i=1, 2, 3, ..., N) may be obtained as the signal information. A histogram of the frequency of peaks versus the heights of FS peaks may be obtained (FIG. 7D), and two populations are distinguished from each other by setting a threshold of FS peak height. The population with peak heights smaller than the threshold is identified as the reference particles, and the number of peaks $N_r'$ and height of each peak ($h_{r(j)}'$, j=1, 2, 3, ..., $N_r'$) may be obtained as the signal information of the reference particles. The average FS peak height of the reference particles $h_{r\,(avg)}'$ may be obtained with equation (1). Meanwhile, the other population with peak heights larger than the threshold is identified as the target particles, and the number of peaks $N_t'$ and height of each peak ($h_{t(k)}'$, k=1, 2, 3, ..., $N_t'$) in this population may be obtained as the signal information of the target particles. The average FS peak height of the target particles $h_{t\,(avg)}'$ may be obtained with equation (2). Accordingly, the average volume of the target particles $V_{t\,(avg)}'$ may be determined by correcting $h_{t\,(avg)}'$ with $h_{r\,(avg)}'$ as shown in the following equation (7) where $V_{r\,(avg)}$ is a known average volume of the reference particles.

$$V'_{t(avg)} = \frac{h_{t(avg)}'}{h_{r(avg)}'} \times V_{r(avg)} \tag{7}$$

The $h_{t\,(avg)}'$ measured in FIG. 7D may be different from the $h_{t\,(avg)}$ measured in FIG. 7B when not all the particles are aligned at the center of the flow cell or the incident light beam has a non-uniform intensity (e.g., higher intensity near the beam center and lower intensity near the edge). When the average FS peak height is used to determine the average volume of the target particles without using reference particles as described in the disclosure, the difference between $h_{t\,(avg)}$ or $h_{t\,(avg)}'$ may result in inconsistent measurements of the average volume of the same target particles. When the flow cell has a cross section size larger than the particles or there is no sheath flow to focus the particles, this misalignment may happen frequently and lead to inconsistent measurements. This inconsistency may be reduced or avoided using a method as described in the disclosure. For example, the determined volume $V_{t\,(avg)}$ may be equal to $V_{t\,(avg)}'$ as shown in the following equation (8). This may be achieved by having a plurality of reference particles and target particles to pass through the flow cell.

$$\frac{h_{t(avg)'}}{h_{r(avg)'}} = \frac{h_{t(avg)}}{h_{r(avg)}} \tag{8}$$

When there is a plurality of particles, their probability of passing through different positions may be determined by the flow velocity profile, which may be the same for both reference particles and target particles.

Besides the peak height and average peak height discussed above, various other types of signal information (e.g., the peak width, the peak area, the distribution of peak heights, and distribution width of peak heights) may also be used for correction to determine the size information of the target particles. For example, as shown in FIG. 7B, the distribution of the FS peak heights for the population of reference particles is $F_r(x)$, and the distribution of the FS peak heights for the population of target particles is $F_t(x)$. The diameter distribution of the target particles $G_t(x)$ may be determined by correcting $F_t(x)$ with $F_r(x)$ as shown in the following equation (9) where the symbol Deconv{ } represents the mathematical operation of deconvolution. The deconvolution results may also be computed using other methods including but not limited to Fourier Transform.

$$G_t(x) = \text{Deconv}\{F_t(x), F_r(x)\} \tag{9}$$

Similarly, as shown in FIG. 7D, the distribution of the FS peak heights for the population of reference particles is $F_r'(x)$, and the distribution of the FS peak heights for the population of target particles is $F_t'(x)$. The diameter distribution of the target particles $G_t'(x)$ may be determined by correcting $F_t'(x)$ with $F_r'(x)$ as shown in the following equation (10).

$$G_t'(x) = \text{Deconv}\{F_t'(x), F_r'(x)\} \tag{10}$$

Similar to the discussions above, when there is a plurality of target particles and reference particles to ensure the requirement of the following equation (11), the determined diameter distributions of the target particles are equal as shown in the following equation (12).

$$\text{Deconv}\{F_t(x), F_r(x)\} = \text{Deconv}\{F_t'(x), F_r'(x)\} \tag{11}$$

$$G_t'(x) = G_t(x) \tag{12}$$

This means that with a method as described herein, the diameter distribution for the same target particles determined in different scenarios is consistent.

Figure 8:
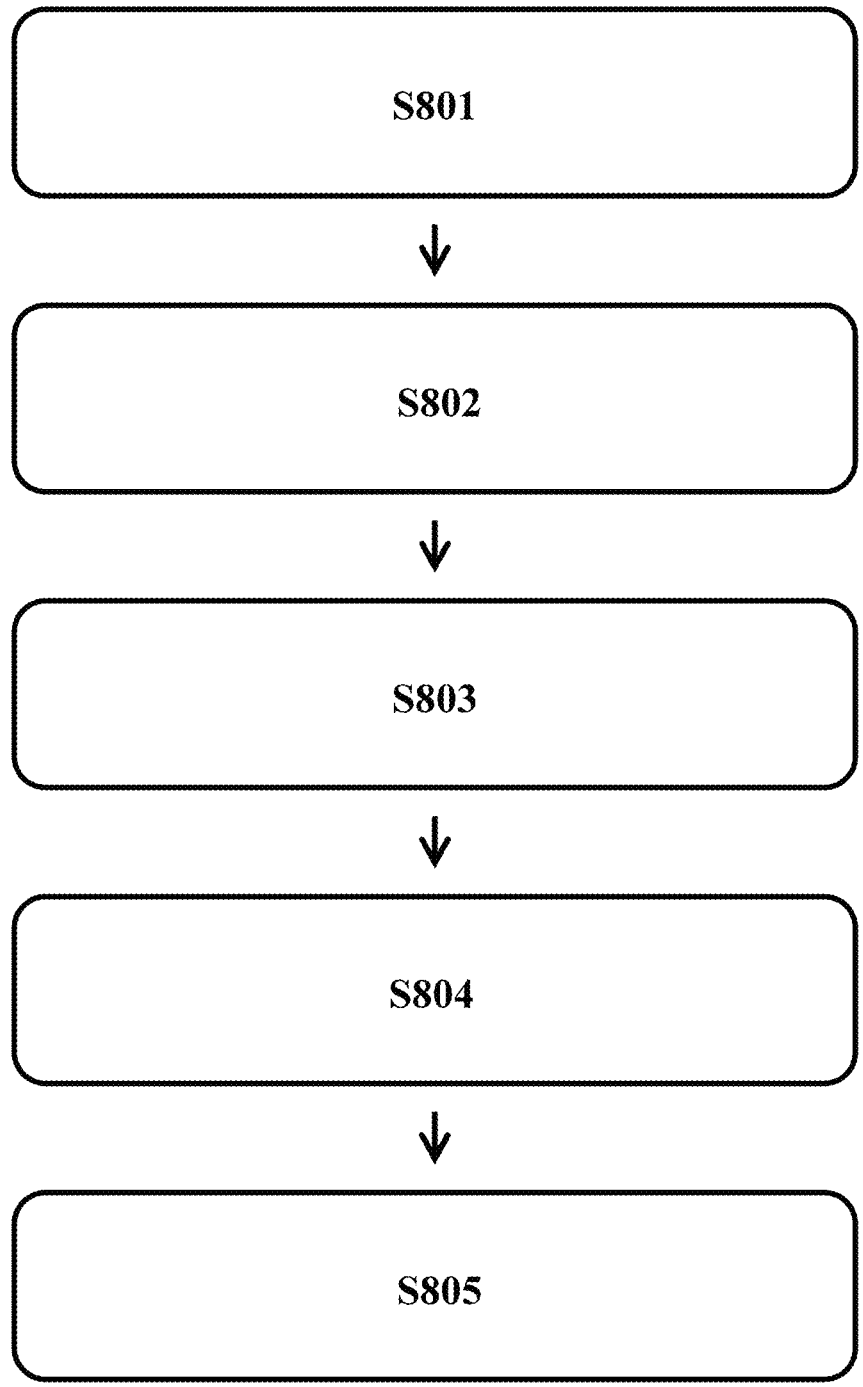
FIG. 8 is a block diagram illustrating a method of determining the size information of blood cells with correction from reference particles according to an embodiment of the disclosure.
Figure 9A:
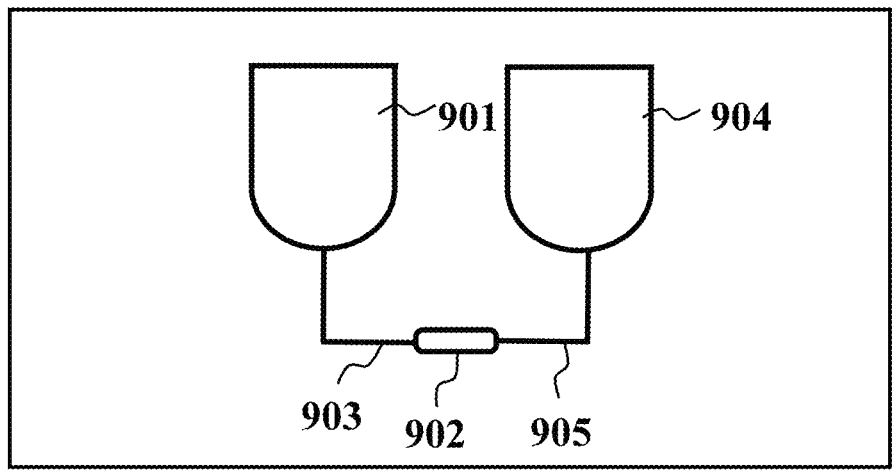
FIG. 9A illustrates an example of a fluidic cartridge for determining the size information of blood cells with correction from reference particles where the fluidic cartridge receives a sample having both blood cells and reference particles (e.g., microbeads) according to an embodiment of the disclosure.

FIG. 8 illustrates a method to determine the size information of blood cells. First in S801, a cartridge receives a sample having blood cells, and the cartridge is placed in an analyzer as described in FIG. 2. Second in S802, the analyzer measures a signal from the blood cells and reference particles in the cartridge. Third in S803, the signal is analyzed to obtain a signal information. Fourth in in S804, the signal information of the blood cells is distinguished from the signal information of the reference particles. Fifth in S805, the size information of the blood cells may be determined by correcting the signal information of the blood cells with the signal information of the reference particles. Examples of the determined size information may include but are not limited to the size of an RBC, the average size of a plurality of RBCs (i.e., Mean Corpuscular Volume (MCV)), the size distribution of a plurality of RBCs (i.e., Red Cell Distribution Width (RDW)), the volume percentage of RBCs in blood (i.e., Hematocrit HCT), the average volume of a plurality of platelets (i.e., Mean Platelet Volume (MPV)), the volume percentage of PLTs in blood (i.e., plateletcrit), et cetera FIG. 9A shows a non-limiting example of a fluidic cartridge as described herein. The fluidic cartridge may include: a first chamber 901 configured for receiving a sample, a flow cell 902 in fluidic connection with the first chamber 901 via a fluidic conduit 903, and a second chamber 904 in fluidic connection with the flow cell 902 via a fluidic conduit 905. A sample received into the first chamber 901 may exit the first chamber 901 and enter the flow cell 902 to be illuminated by an incident light beam. A signal may be measured from the sample in the flow cell and analyzed by an analyzer. The sample exiting the flow cell 902 may be collected in the second chamber 904. A pneumatic pressure may be applied to the first chamber 901 to drive the sample to enter the flow cell 902 for the signal measurement. As alternatives to the pneumatic pressure, various other types of driving mechanisms may be used, and non-limiting examples of those driving mechanisms may include but are not limited to gravity, capillary force, electrophoresis, and centrifugal force, et cetera In this example, a sample having target particles (e.g., blood cells) and reference particles may be received into the first chamber 901.

Figure 9B:
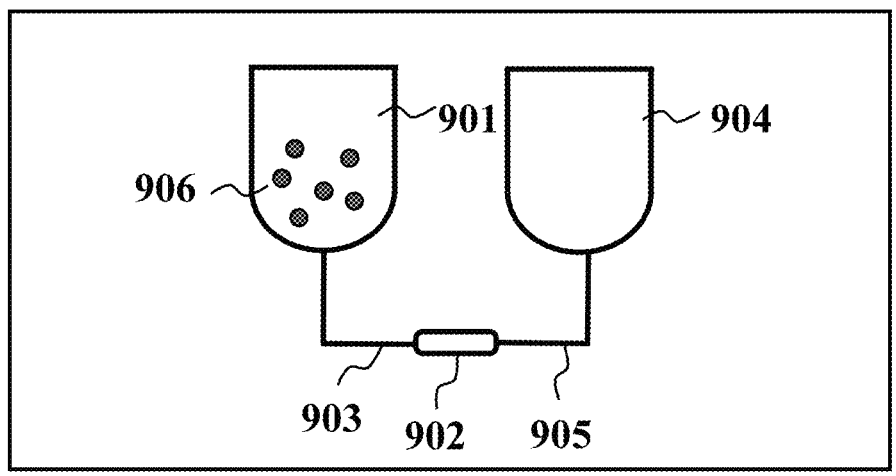
FIG. 9B illustrates another example of a fluidic cartridge for determining the size information of blood cells with correction from reference particles where the fluidic cartridge contains reference particles (e.g., microbeads), receives a sample having blood cells, and forms a sample mixture of the blood cells and reference particles according to an embodiment of the disclosure.

FIG. 9B shows another non-limiting example of a fluidic cartridge as described herein. In this example, the first chamber 901 contains reference particles 906 (e.g., microbeads). A sample having target particles (e.g., blood cells) may be received into the first chamber 901 and mixed with the reference particles 906 to form a sample mixture. This sample mixture is then measured in the flow cell 902.

Figure 9C:
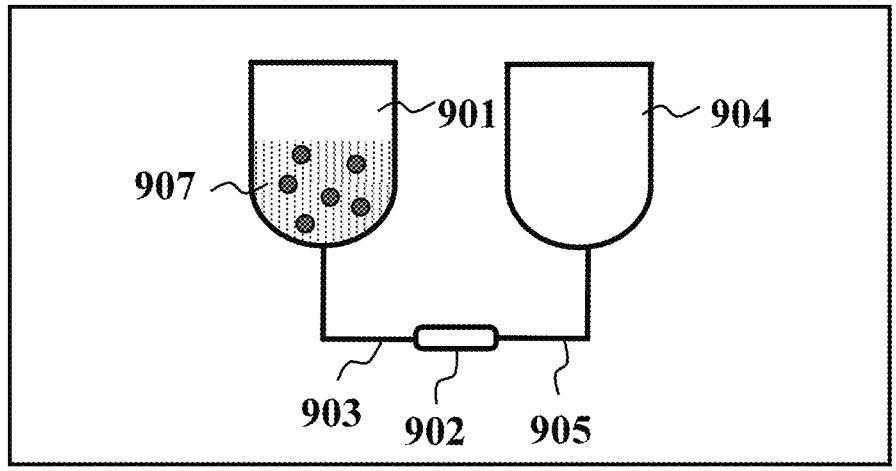
FIG. 9C illustrates another example of a fluidic cartridge for determining the size information of blood cells with correction from reference particles where the fluidic cartridge contains a reagent having reference particles (e.g., microbeads), receives a sample having blood cells, and forms a sample mixture of the blood cells and reference particles according to an embodiment of the disclosure.

FIG. 9C shows another non-limiting example of a fluidic cartridge as described herein. In this example, the first chamber 901 contains a reagent 907 having reference particles (e.g., microbeads). First, the reagent 907 having reference particles may be measured in the flow cell 902 and collected into the second chamber 904. Second, a sample having target particles (e.g., blood cells) may be received into the first chamber 901 and is then measured in the flow cell 902. A signal is measured from the reagent 907 having reference particles and another signal is measured from the sample having target particles (e.g., blood cells).

Figure 9D:
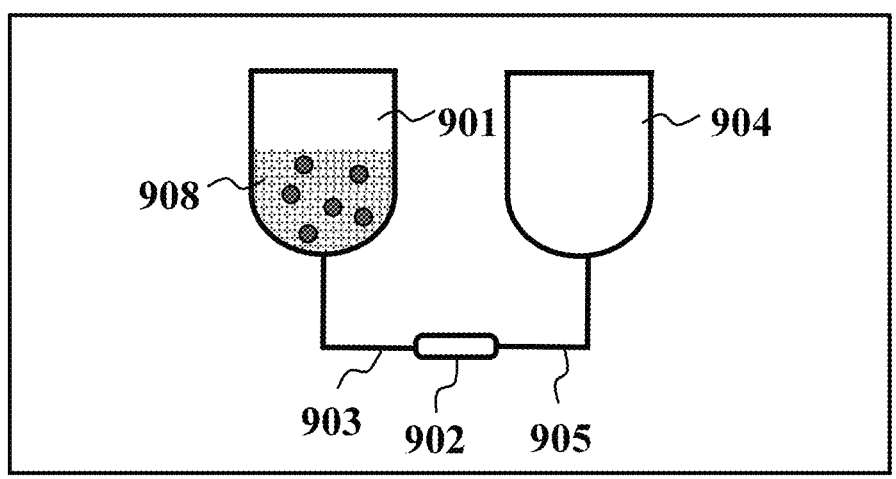
FIG. 9D illustrates another example of a fluidic cartridge for determining the size information of blood cells with correction from reference particles where the fluidic cartridge contains a reagent having reference particles (e.g., microbeads) and a surfactant according to an embodiment of the disclosure.
Figure 10A:
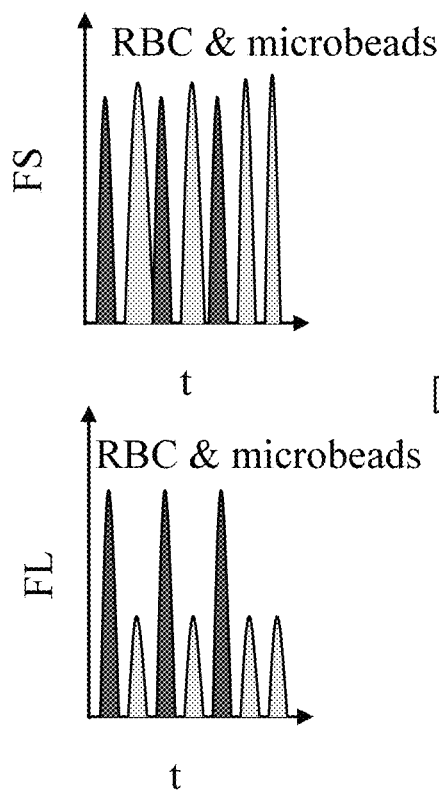
FIGS. 10A-10C illustrate an example of determining the size information of blood cells with correction where the target particles are RBCs and the reference particles are microbeads according to an embodiment of the disclosure.
Figure 10B:
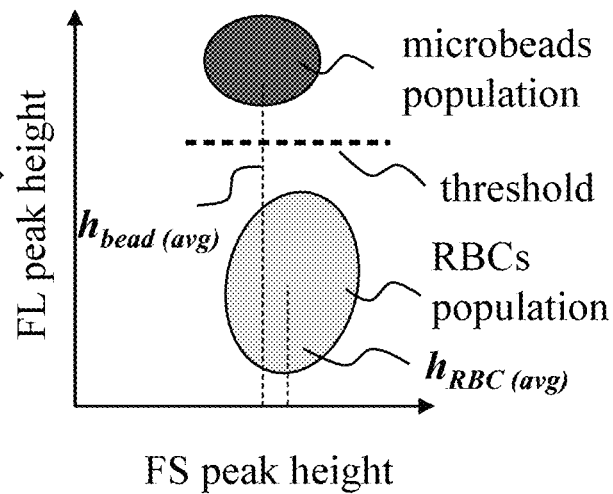
Figure 10C:
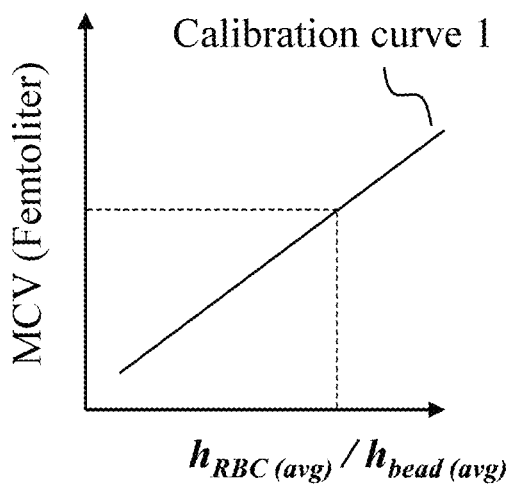

FIG. 9D shows another non-limiting example of a fluidic cartridge as describe herein. In this example, the first chamber 901 contains a reagent 908 having reference particles (e.g., microbeads) and a surfactant. Examples of the surfactant may include but are not limited to dodecyl trimethyl ammonium chloride, decyl trimethyl ammonium chloride, sodium dodecyl sulfate, et cetera FIGS. 10A-10C show a non-limiting example of a method of determining the size information of blood cells. In this example, the blood cells are RBCs and the reference particles are microbeads. First, a sample having a plurality of RBCs is received into a fluidic cartridge as described in FIG. 9B and forms a sample mixture with the microbeads in the fluidic cartridge. The fluidic cartridge is placed in an analyzer. When a stream of the sample mixture including the RBCs and microbeads passes through the flow cell, an FS signal and an FL signal are simultaneously measured by the analyzer (FIG. 10A). Each pair of an FS peak and an FL peak represents an RBC or a microbead detected in the stream of the sample mixture. The number of FS peaks $N_{FS}$ and height of each FS peak ($h_i$, i=1, 2, 3, . . . , $N_{FS}$) may be obtained as the signal information of this FS signal. The number of FL peaks $N_{FL}$ and height of each FL peak ($l_i$, i=1, 2, 3, . . . , $N_{FL}$, $N_{FL}=N_{FS}$) may be obtained as the signal information of this FL signal. A scatter plot of the FL peak height $l_i$ versus the FS peak height $h_i$ may be obtained (FIG. 10B). Two populations are distinguished from each other by setting a threshold of FL peak height in the scatter plot. The population with FL peak height larger than the threshold is from the microbeads. This is achieved by using microbeads with an FL intensity stronger than RBCs. The number of FS peaks $N_{bead}$ and height of each FS peak ($h_{bead\ (j)}$, j=1, 2, 3, . . . , $N_{bead}$) in this population may be obtained as the FS signal information of microbeads. Additionally, the average FS peak height of the microbeads $h_{bead\ (avg)}$ may be calculated according to the following equation (13).

$$h_{bead(avg)} = \frac{\sum_{j=1}^{N_{bead}} h_{bead(j)}}{N_{bead}} \quad (13)$$

Meanwhile, the other population with FL peak heights smaller than the threshold is the RBCs. The number of FS peaks $N_{RBC}$ and height of each FS peak ($h_{RBC\ (k)}$, k=1, 2, 3, . . . , $N_{RBC}$) in this population may be obtained as the FS signal information of RBCs. Similarly, the average FS peak height of the RBCs $h_{RBC\ (avg)}$ may be calculated according to the following equation (14).

$$h_{RBC(avg)} = \frac{\sum_{k=1}^{N_{RBC}} h_{RBC(k)}}{N_{RBC}} \quad (14)$$

MCV of the sample may be calculated by correcting $h_{RBC\ (avg)}$ with $h_{bead\ (avg)}$ in as shown in the following equation (15) where a is a known constant in a predetermined calibration curve 1 for MCV (FIG. 10C).

$$MCV = a \times \frac{h_{RBC(avg)}}{h_{bead(avg)}} \quad (15)$$

Additionally, HCT of the sample may be determined as shown in the following equation (16) where $V_s$ is a known volume of the sample received into the fluidic cartridge.

$$HCT = MCV \times \frac{N_{RBC}}{V_s} \times 100\% \quad (16)$$

Figure 11A:
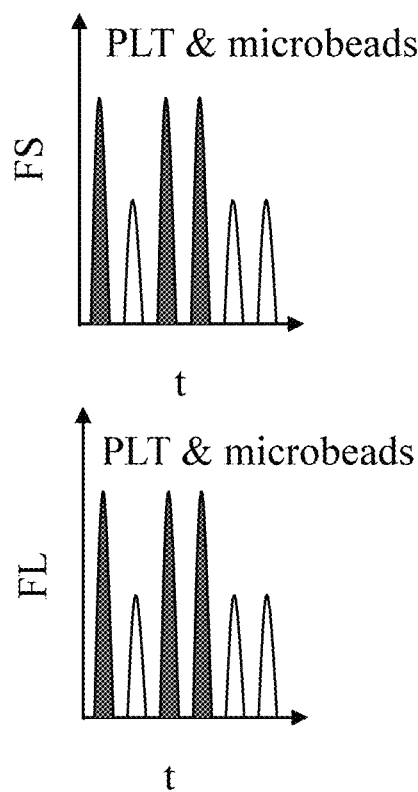
FIGS. 11A-11C illustrate another example of determining the size information of blood cells with correction where the target particles are PLTs and the reference particles are microbeads according to an embodiment of the disclosure.
Figure 11B:
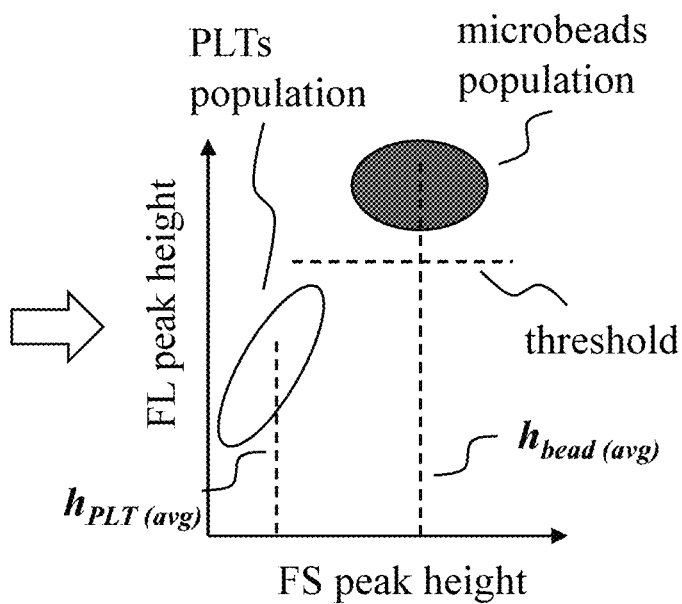
Figure 11C:
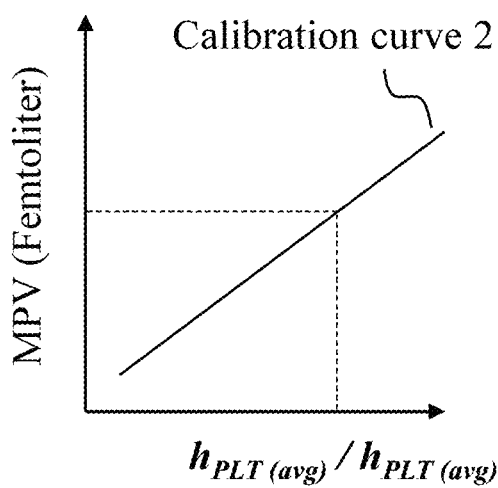

FIGS. 11A-11C show another non-limiting example of a method of determining the size information of blood cells. In this example, the blood cells are PLTs and the reference particles are microbeads. First, a sample with a plurality of PLTs is received into a fluidic cartridge as described in FIG. 9B and forms a sample mixture with the microbeads in the fluidic cartridge. The fluidic cartridge is placed in an analyzer. When a stream of the sample mixture including the PLTs and microbeads passes through the flow cell, an FS signal and an FL signal are simultaneously measured by the analyzer (FIG. 11A). Each pair of an FS peak and an FL peak represents a PLT or a microbead in the stream of the sample mixture. The number of FS peaks $N_{FS}$ and height of each FS peak ($h_i$, i=1, 2, 3, . . . , $N_{FS}$) may be obtained as the signal information of this FS signal. The number of FL peaks $N_{FL}$ and height of each FL peak ($l_i$, i=1, 2, 3, . . . , $N_{FL}$, $N_{FL}$=$N_{FS}$) may be obtained as the signal information of this FL signal. A scatter plot of the FL peak height $l_i$ versus the FS peak height $h_i$ may be obtained (FIG. 11B). Two populations may be distinguished from each other by setting a threshold of FL peak height in the scatter plot. The population with FL peak height larger than the threshold is from the microbeads, because the microbeads used in the fluidic cartridge have an FL intensity stronger than PLTs. The number of FS peaks $N_{bead}$ and height of each FS peak ($h_{bead\ (j)}$, j=1, 2, 3, . . . , $N_{bead}$) in this population may be obtained as the FS signal information of microbeads. Additionally, the average FS peak height of the microbeads $h_{bead\ (avg)}$ may be obtained with equation (13). Meanwhile, the other population with FL peak heights smaller than the threshold is from the PLTs. The number of FS peaks $N_{PLT}$ and height of each FS peak ($N_{PLT\ (k)}$, k=1, 2, 3, . . . , $N_{PLT}$) in this population may be obtained as the FS signal information of PLTs. Similarly, the average FS peak height of the PLTs $h_{PLT\ (avg)}$ may be calculated according to the following equation (17).

$$h_{PLT(avg)} = \frac{\sum_{k=1}^{N_{PLT}} h_{PLT(k)}}{N_{PLT}} \quad (17)$$

The MPV of the sample may be calculated by correcting $h_{PLT\ (avg)}$ with $h_{bead\ (avg)}$ according to the following equation (18) where b is a constant in a predetermined calibration curve 2 for MPV (FIG. 11C).

$$MPV = b \times \frac{h_{PLT(avg)}}{h_{bead(avg)}} \quad (18)$$

Additionally, with a known volume $V_s$ of the sample received into the fluidic cartridge, plateletcrit of the sample may be determined by the following equation (19).

$$Plateletcrit = \left(\frac{MPV \times N_{PLT}}{V_s}\right) \times 100\% \quad (19)$$

FIGS. 12A-12B show still another non-limiting example of a method of determining the size information of blood cells. In this example, the blood cells are RBCs and PLTs while the reference particles are microbeads. First, a sample having a plurality of RBCs and PLTs is received into a fluidic cartridge as shown in FIG. 9B and forms a sample mixture with the microbeads in the fluidic cartridge. The fluidic cartridge is placed in an analyzer. When a stream of the sample mixture having RBCs, PLTs, and microbeads passes through the flow cell, an FS signal and an FL signal are simultaneously measured by the analyzer (FIG. 12A). Each pair of an FS peak and an FL peak corresponds to an RBC, a PLT or a microbead in the stream of the sample mixture. The number of FS peaks $N_{FS}$ and height of each FS peak ($h_{(i)}$, i=1, 2, 3, . . . , $N_{FS}$) may be obtained as the signal information. The number of FL peaks $N_{FL}$ and height of each FL peak ($l_{(i)}$, i=1, 2, 3, . . . , $N_{FL}$) may be obtained as the signal information. A scatter plot of the FL peak height $l_i$ versus the FS peak height $h_i$ may be obtained (FIG. 12B). Three populations may be distinguished from one another by setting a threshold 1 of FS peak height and a threshold 2 of FL peak height in the scatter plot. The population with FS peak height larger than the threshold 1 and FL peak height smaller than the threshold 2 is from RBCs. The population with FS peak height smaller than the threshold 1 is from PLTs. The population with FS peak height larger than the threshold 1 and the FL peak height larger than the threshold 2 is from microbeads. This separation is achieved by using microbeads having a size larger than PLTs while having an FL intensity stronger than RBCs. The number of FS peaks $N_{RBC}$ and height of each FS peak ($h_{RBC\ (j)}$, j=1, 2, 3, . . . , $N_{RBC}$) in the RBC population may be obtained as the FS signal information of RBCs. Additionally, the average FS peak height of the RBCs $h_{RBC\ (avg)}$ may be obtained with equation (14). The number of FS peaks $N_{PLT}$ and height of each FS peak ($h_{PLT\ (k)}$, k=1, 2, 3, . . . , $N_{PLT}$) in the PLT population may be obtained as the FS signal information of PLTs. Additionally, the average FS peak height of the microbeads $h_{PLT\ (avg)}$ may be obtained with equation (17). The number of FS peaks $N_{bead}$ and height of each FS peak ($h_{bead\ (m)}$, m=1, 2, 3, . . . , $N_{bead}$) in the microbead population may be obtained as the FS signal information of the microbeads. Additionally, the average FS peak height of the microbeads $h_{bead\ (avg)}$ may be obtained with equation (13). Accordingly, MCV of the sample may be determined with the equation (15), and HCT of the sample may be determined with the equation (16). Meanwhile, MPV of the sample may be determined with the equation (18), and plateletcrit of the sample may be determined with the equation (19).

Figure 13A:
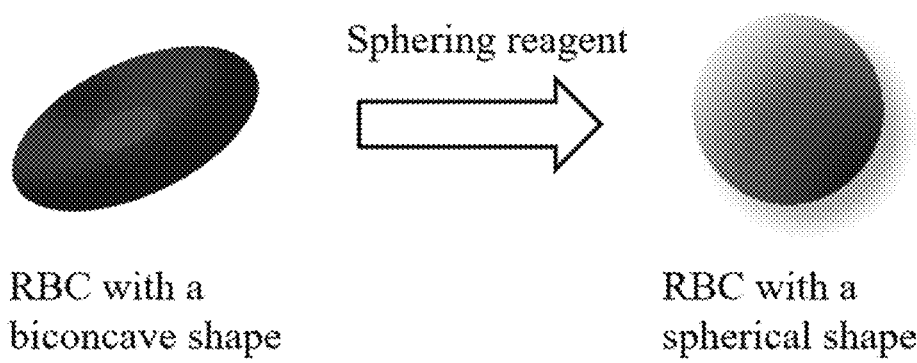
FIGS. 13A-13C illustrate an example of determining the size information of blood cells with correction where the cartridge contains a reagent having microbeads and a surfactant according to an embodiment of the disclosure.
Figure 13B:
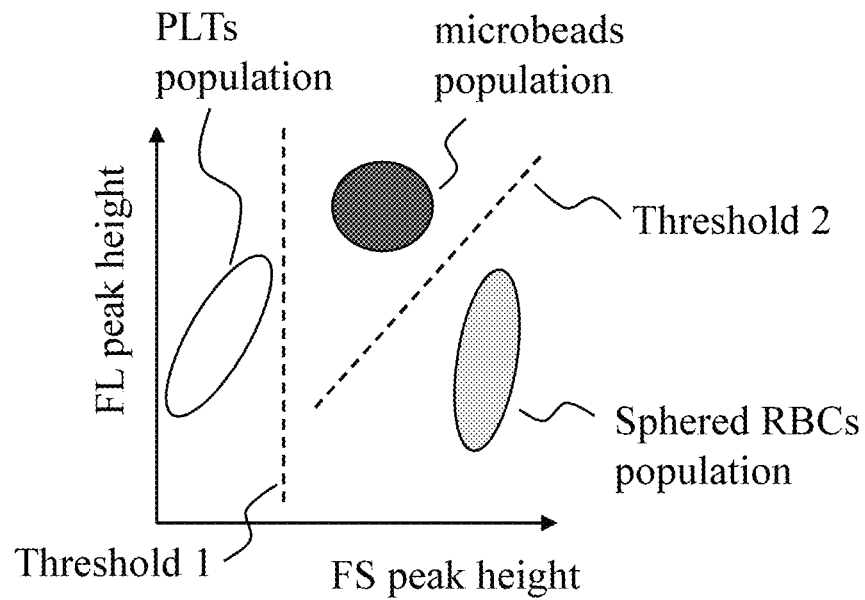

FIGS. 13A-13B show still another non-limiting example of a method of determining the size information of blood cells. In this example, the blood cells are RBCs and PLTs while the reference particles are microbeads. First, a sample having a plurality of RBCs and PLTs is received into a fluidic cartridge as shown in FIG. 9D and forms a sample mixture with the microbeads and the surfactant in the fluidic cartridge. The surfactant is used for two purposes. First, it helps prevent the microbeads from aggregation during the storage in the fluidic cartridge and during the measurement in the flow cell. Second, it changes the RBCs from biconcave shapes into spherical shapes and hence sphered RBCs are measured in the flow cell (FIG. 13A). The fluidic cartridge is placed in an analyzer. When a stream of the sample mixture having RBCs, PLTs, and microbeads passes through the flow cell, an FS signal and an FL signal are simultaneously measured by the analyzer. Each pair of an FS peak and an FL peak corresponds to an RBC, a PLT or a microbead in the stream of the sample mixture. The number of FS peaks $N_{FS}$ and height of each FS peak ($h_{(i)}$, i=1, 2, 3, . . . , $N_{FS}$) may be obtained as the FS signal information. The number of FL peaks $N_{FL}$ and height of each FL peak ($l_{(i)}$, i=1, 2, 3, . . . , $N_{FL}$) may be obtained as the FL signal information. A scatter plot of the FL peak height $l_i$ versus the FS peak height $h_i$ may be obtained (FIG. 13B).

Figure 13C:
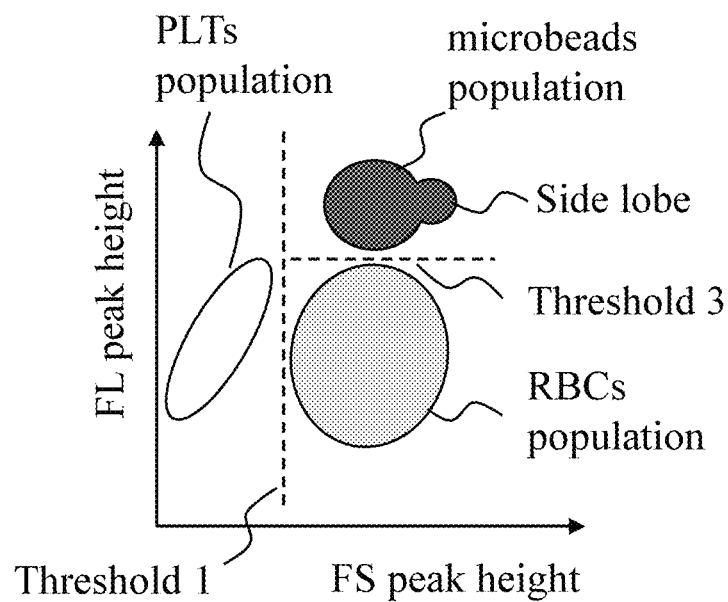

For comparison, another scatter plot may be obtained from the same sample without using the surfactant (FIG. 13C). The population of the microbead particles has a side lobe in FIG. 13C but not in FIG. 13B. This side lobe is caused by aggregation of microbeads without the surfactant. Additionally, the FS signal from the sphered RBCs in FIG. 13B have larger FS peak heights than the FS signal from the biconcave RBCs in FIG. 13C, and as a result, a threshold 2 in FIG. 13B may achieve a clearer separation of the RBCs from the microbeads than the threshold 3 in FIG. 13C. Moreover, the FS peak heights from the sphered RBCs have a narrower distribution than the FS peak heights from the biconcave RBCs, and more accurate signal information of the RBCs may be obtained when determining the size information of the blood cells such as MCV and HCT, et cetera Table 1 shows a comparison of the size information of blood cells measured with or without the method described in this disclosure. Three replicates were measured for a sample having RBCs. MCV and HCT were determined following the example shown in FIGS. 10A-10C. Coefficient of variation (CV) of the three replicates was calculated as shown in Table 1. The CV of the HCT measurements decreases from 9.3% to 0.9% with the disclosed method. The CV of the MCV measurements decreases from 5.1% to 1.5% with the disclosed method. These results indicate that the size information of blood cells may be determined more accurately with a method as described in the disclosure.

TABLE 1

| Sample | HCT (%) without the disclosed method | MCV (fL) without the disclosed method | HCT (%) with the disclosed method | MCV (fL) with the disclosed method |
|---|---|---|---|---|
| Replicate 1 | 42.6 | 89.3 | 43.5 | 92.0 |
| Replicate 2 | 48.1 | 95.3 | 43.9 | 93.2 |
| Replicate 3 | 40.1 | 86.3 | 43.1 | 90.5 |
| CV of 3 replicates | 9.3% | 5.1% | 0.9% | 1.5% |

Figure 14A:
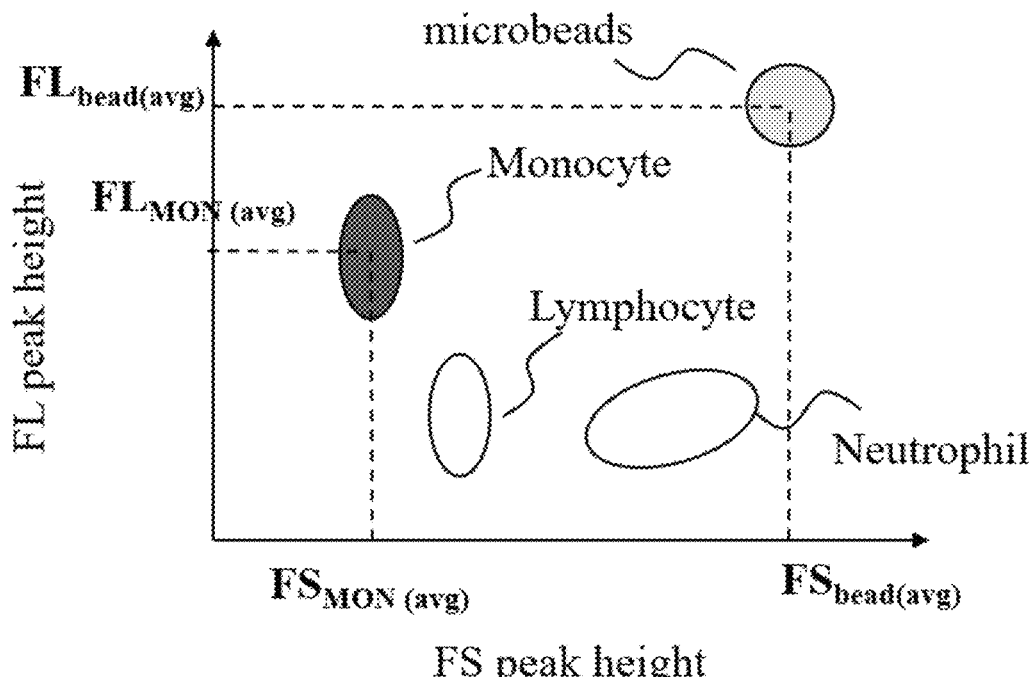
FIGS. 14A-14B illustrate an example of determining the size information of blood cells with correction where the cartridge contains a reagent having microbeads and a fluorescent dye according to an embodiment of the disclosure.
Figure 14B:
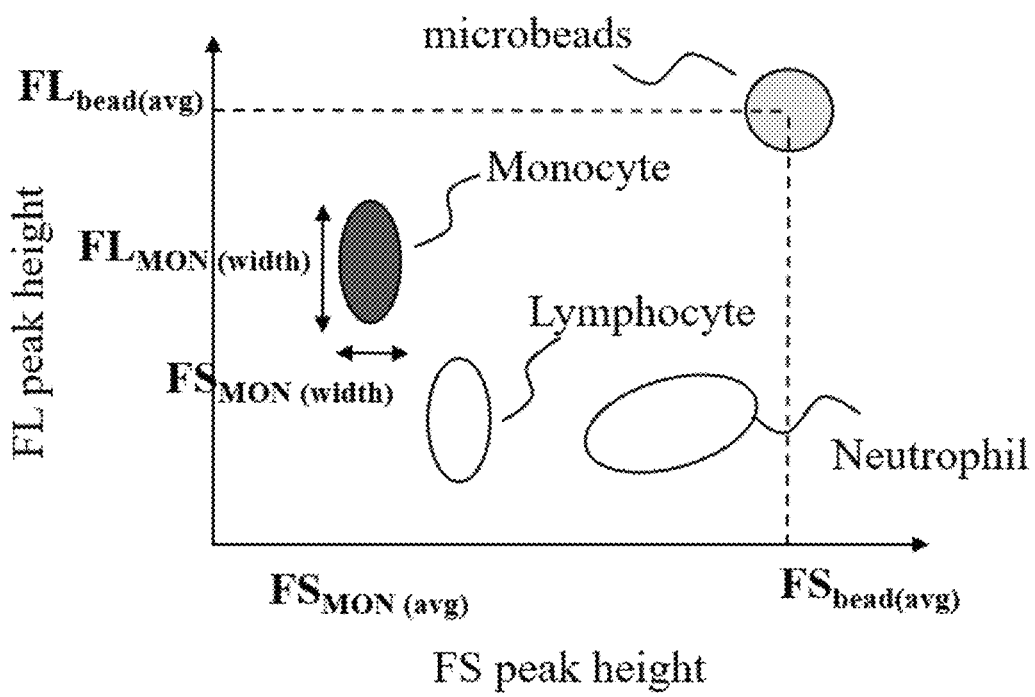

FIGS. 14A-14B show another example of a method of determining the size information of blood cells. In this example, the blood cells are White Blood Cells (WBCs) while the reference particles are microbeads. First, a sample having a plurality of WBCs is received into a fluidic cartridge as shown in FIG. 9C. The sample is received into the chamber 901, which contains a reagent 907 having the microbeads and a fluorescent dye. The fluorescent dye is used to selectively labels the WBCs by binding to the nucleic acids. Example of the fluorescent dye may include but not limit to Acridine Orange, Basic Orange 21, et cetera The fluidic cartridge is then placed into an analyzer. The analyzer provides an actuation method to drive the fluid transfer in the cartridge. With the actuation method, the received sample, and the reagent 907 forms a sample mixture in the chamber 901. The sample mixture is further transferred and measured in the flow cell 902, which may be a shealthless flow cell, where an FS signal and an FL signal are simultaneously measured by the analyzer (FIG. 14A).

In FIG. 14A, each pair of an FS peak and an FL peak corresponds to an WBC or a microbead in the stream of the sample mixture. Similar to the example in FIG. 13B, the microbeads population may be distinguished from the WBCs by setting a threshold of FS, a threshold of FL or a combination of FS and FL. Meanwhile, the WBCs may be distinguished into sub-populations, including lymphocyte, monocyte, and neutrophil, by different level of F S and FL. The averaged FS and FL peak heights of the microbeads, $FS_{bead(avg)}$ and $FL_{bead(avg)}$ may be obtained from the measurement signals. This signal information of the microbeads may then be used to correct the size information of the blood cells. For example, the averaged FS and FL peak heights of the monocyte sub-population, $FS_{MON(avg)}$ and $FL_{MON(avg)}$ may be corrected according to the following equations (20) and (21).

$$FS'_{MON(avg)} = \frac{FS_{MON(avg)}}{FS_{bead(avg)}} \quad (20)$$

$$FL'_{MON(avg)} = \frac{FL_{MON(avg)}}{FL_{bead(avg)}} \quad (21)$$

In the above equations (20) and (21), $FS'_{MON(avg)}$ and $FL'_{MON(avg)}$ are corrected peak heights of the monocyte sub-population. $FS'_{MON(avg)}$ may be used as quantitative measurement of monocyte cells size, as forward light scattering signal intensity is proportional to cell size. $FL'_{MON(avg)}$ may also be used as a quantitative measurement of size of monocyte cells (Susan A. Moore, Cell size specific binding of the fluorescent dye calcofluor to budding yeast, Biochimica at Biophysica Acta, Vol. 1035, 1990, Pages 206-213).

For another example, as shown in FIG. 14. B, the distribution width of the monocyte sub-population in FS and FL peak heights, $FS_{MON(width)}$, and $FL_{MON(width)}$ may be corrected according to the following equations (22) and (23).

$$FS'_{MON(width)} = \frac{FS_{MON(width)}}{FS_{bead(avg)}} \quad (22)$$

$$FL'_{MON(width)} = \frac{FL_{MON(width)}}{FL_{bead(avg)}} \quad (23)$$

In the above equations (22) and (23), $FS'_{MON(width)}$ and $FL'_{MON(width)}$ are corrected distribution width of the monocyte sub-population in FS and FL peak heights. Similarly, they may be used as size measurements of the monocyte cells, e.g., the Monocyte Distribution Width (MDW) of the monocyte cells.

The size measurements of monocyte cells, such as the averaged size of the monocyte cells and the Monocyte Distribution Width (MDW), have been shown to be a useful clinical biomarker (US Patent Application: US2019/0324035 A1). However, the measurement is very sensitive to the analyzer performance drift, e.g., drift of the alignment between a laser spot and a flow cell for the monocyte measurement. Therefore, constant and frequent system calibration is required to maintain the measurement accuracy. By using the measurement of a reference particle, e.g., microbeads, to correct the measures of the monocyte cells, the burden of system calibration may be avoided, and make it possible to measure this clinical biomarker in point-of-care settings, such as hospital emergency rooms.

Many different arrangements of the various components depicted, as well as components not shown, are possible without departing from the spirit and scope of the disclosure. Embodiments of the disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

The disclosure claimed is:

1. A method comprising the steps of:
    measuring a signal from a target particle and a reference particle in a cartridge device, wherein
        the cartridge device is received into an analyzer to perform the measurement of the signal, and
        the signal is measured from the target particle and the reference particle when they flow through a flow cell in the cartridge device;
    analyzing the measured signal to obtain signal information of the target particle and signal information of the reference particle; and
    determining size information of the target particle by correcting the signal information of the target particle with the signal information of the reference particle.

2. The method of claim 1, wherein the reference particle has a known size.

3. The method of claim 1, wherein two or more types of signals are measured to distinguish the signal information of the target particle from the signal information of the reference particle.

4. The method of claim 1, wherein:
    the measured signal comprises an optical signal, an electrical signal, an acoustic signal, a magnetic signal, or a combination thereof; and
    the optical signal comprises a forward scattering signal, a fluorescence signal, or a combination thereof.

5. The method of claim 1, wherein the obtained signal information comprises a peak height, a peak width, a peak area, an averaged peak height, an average peak width, an average peak area, a distribution of peak heights, a distribution of peak widths, a distribution of peak areas, a distribution width of peak heights, or a combination thereof.

6. The method of claim 1, wherein the determined size information comprises a particle diameter, a particle volume, an average particle diameter, an average particle volume, a distribution of particle diameters, a distribution of particle volumes, or a combination thereof.

7. The method of claim 1, wherein the flow cell is a sheathless flow cell.

8. The method of claim 1, wherein the reference particle and the target particle form a sample mixture in the cartridge device before flowing through the flow cell.

9. The method of claim 1, wherein:
    the cartridge further contains a fluorescent dye configured to label the target particles or a surfactant; and
    the sample mixture comprises:
        (a) a combination of the fluorescent dye, the reference particle, and the target particle, or
        (b) a combination of the surfactant, the reference particle, and the target particle.

10. The method of claim 9, wherein:
    the surfactant is configured to change a shape of the target particle to spherical; and
    the fluorescent dye is configured to label the target particle.

11. The method of claim 1, wherein the target particle is a blood cell.

12. The method of claim 1, wherein the determined size information comprises at least one item selected from the list consisting of: Mean Corpuscular Volume (MCV), Red Cell Distribution Width (RDW)), Hematocrit (HCT), Mean Platelet Volume (MPV), Platelet Distribution Width (PDW), plateletcrit, averaged size of Monocyte, and Monocyte width distribution (MWD) of a sample comprising blood cells.

13. The method of claim 1, wherein the step of correcting the signal information of the target particle with the signal information of the reference particle further comprises a step of dividing a signal peak of the target particle by a signal peak of the reference particle.

14. The method of claim 13, wherein:
    the signal peak of the target particle is selected from the group consisting of a forward scattering (FS) peak height of the target particle and a fluorescence (FL) peak height of the target particle; and
    the single peak of the reference particle is selected from the group consisting of a FS peak height of the reference particle and a FL peak height of the reference particle.

15. The method of claim 1, wherein the step of correcting the signal information of the target particle with the signal information of the reference particle further comprises a step of dividing an average signal peak of multiple target particles by an average signal peak of multiple reference particles.

16. The method of claim 15, wherein:
    the average signal peak of the multiple target particles is selected from the group consisting of an average forward scattering (FS) peak height of the multiple target particles and an average fluorescence (FL) peak height of the multiple target particles; and
    the average signal peak of the multiple reference particles is selected from the group consisting of an average FS peak height of the multiple reference particles and an average FL peak height of the multiple reference particles.

17. The method of claim 1, wherein the step of correcting the signal information of the target particle with the signal information of the reference particle comprises a step of dividing a distribution width of multiple target particles by an average signal peak of multiple reference particles.

18. The method of claim 17, wherein:
    the distribution width of the multiple target particles is selected from the group consisting of the distribution width of the target particles in forward scattering (FS) peak heights and the distribution width of the target particles in fluorescence (FL) peak heights; and
    the average signal peak of the multiple reference particles is selected from the group consisting of an average FS peak height and an average FL peak height.

19. The method of claim 1, wherein the step of correcting the signal information of the target particle with the signal information of the reference particle further comprises a step of dividing a signal peak of the target particle by an average signal peak of multiple reference particles.

20. The method of claim 19, wherein:
    the signal peak of the target particle is selected from the group consisting of a forward scattering (FS) peak height of the target particle and a fluorescence (FL) peak height of the target particle; and
    the average signal peak of the multiple reference particles is selected from the group consisting of an average FS peak height of the multiple reference particles and an average FL peak height of the multiple reference particles.

* * * * *